(12) United States Patent
Newman et al.

(10) Patent No.: US 11,300,565 B2
(45) Date of Patent: Apr. 12, 2022

(54) EXOSOME-MEDIATED DIAGNOSIS OF HUMAN IMMUNODEFICIENCY VIRUS INFECTION

(71) Applicant: MOREHOUSE SCHOOL OF MEDICINE, Atlanta, GA (US)

(72) Inventors: Gale W. Newman, Duluth, GA (US); Sam Anyanwu, Atlanta, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

(21) Appl. No.: 16/601,178

(22) Filed: Oct. 14, 2019

(65) Prior Publication Data
US 2020/0033343 A1 Jan. 30, 2020

Related U.S. Application Data

(63) Continuation of application No. 15/377,054, filed on Dec. 13, 2016, now Pat. No. 10,495,640, which is a
(Continued)

(51) Int. Cl.
*C12Q 1/70* (2006.01)
*G01N 33/53* (2006.01)
(Continued)

(52) U.S. Cl.
CPC ......... *G01N 33/56988* (2013.01); *C12Q 1/70* (2013.01); *C12Q 1/703* (2013.01);
(Continued)

(58) Field of Classification Search
None
See application file for complete search history.

(56) References Cited

U.S. PATENT DOCUMENTS

| 6,048,685 A | 4/2000 | Alizon et al. |
| 6,287,759 B1 | 9/2001 | Tsarev et al. |

(Continued)

FOREIGN PATENT DOCUMENTS

| EP | 0400548 | 5/1990 |
| WO | 2005121369 | 12/2005 |

(Continued)

OTHER PUBLICATIONS

Dimov, I., et al., "Urinary exosomes", The Scientific World Journal, vol. 9, pp. 1107-1118, (2009).
(Continued)

*Primary Examiner* — M Franco G Salvoza
(74) *Attorney, Agent, or Firm* — Ping Wang; Rimon Law

(57) ABSTRACT

A method for diagnosing hepatitis virus infection or a hepatitis disease condition in a subject based on hepatitis virus-associated biomarkers present on exosomes in a bodily fluid sample from the subject is disclosed. Also disclosed are a method for monitoring the course of a hepatitis virus infection or a hepatitis disease condition in a subject and a method for monitoring effectiveness of treatment to a subject with an anti-hepatitis virus agent based on hepatitis virus-associated biomarkers present on exosomes in bodily fluid samples from the subject, as well as a kit for diagnosing hepatitis virus infection and/or a hepatitis disease condition in a subject based on hepatitis virus-associated biomarkers on exosomes in bodily fluid samples from the subject.

20 Claims, 11 Drawing Sheets

Specification includes a Sequence Listing.

Related U.S. Application Data continuation of application No. 15/270,848, filed on Sep. 20, 2016, now Pat. No. 10,416,161, which is a continuation of application No. 14/159,612, filed on Jan. 21, 2014, now Pat. No. 9,487,837, which is a continuation-in-part of application No. 12/572,652, filed on Oct. 2, 2009, now Pat. No. 10,545,149.

(60) Provisional application No. 61/102,941, filed on Oct. 6, 2008.

(51) Int. Cl.
| | |
|---|---|
| G01N 33/569 | (2006.01) |
| G01N 33/493 | (2006.01) |
| G01N 33/68 | (2006.01) |
| G01N 33/576 | (2006.01) |
| G01N 1/40 | (2006.01) |

(52) U.S. Cl.
CPC ............ *C12Q 1/706* (2013.01); *C12Q 1/707* (2013.01); *G01N 33/493* (2013.01); *G01N 33/56983* (2013.01); *G01N 33/576* (2013.01); *G01N 33/6893* (2013.01); *G01N 1/40* (2013.01); *G01N 2333/02* (2013.01); *G01N 2333/10* (2013.01); *G01N 2333/161* (2013.01); *G01N 2333/162* (2013.01); *G01N 2333/163* (2013.01); *G01N 2333/186* (2013.01); *G01N 2800/347* (2013.01); *G01N 2800/52* (2013.01); *G01N 2800/56* (2013.01); *Y02A 50/30* (2018.01)

(56) References Cited

U.S. PATENT DOCUMENTS

| | | |
|---|---|---|
| 6,451,578 B1 | 9/2002 | Simons et al. |
| 7,198,923 B1 | 4/2007 | Abrignani et al. |
| 2004/0241176 A1 | 12/2004 | Lamparski et al. |
| 2006/0252075 A1 | 11/2006 | Zagury et al. |
| 2008/0107625 A1 | 5/2008 | D'Andrea et al. |
| 2009/0078638 A1 | 3/2009 | Bonhomme et al. |
| 2009/0136515 A1 | 5/2009 | Matsumori |
| 2009/0220944 A1 | 9/2009 | Fais et al. |
| 2010/0196426 A1 | 8/2010 | Skog et al. |
| 2010/0203529 A1 | 8/2010 | Kuslich et al. |
| 2010/0298151 A1 | 11/2010 | Taylor et al. |
| 2011/0053157 A1 | 3/2011 | Skog et al. |
| 2012/0077263 A1 | 3/2012 | Ward et al. |
| 2013/0178383 A1 | 7/2013 | Spetzler et al. |

FOREIGN PATENT DOCUMENTS

| | | |
|---|---|---|
| WO | 2007015174 | 2/2007 |
| WO | 2007/103572 | 9/2007 |
| WO | 2007127848 | 11/2007 |
| WO | 2009092386 | 7/2009 |

OTHER PUBLICATIONS

Hoorn, E.J., et al., "Prospects for urinary proteomics: exosomes as a source of urinary biomarkers", Nephrology, vol. 10, pp. 283-290, (2005).
Campbell, T.D., et al., "HIV-1 Nef protein is secreted into vesicles that can fuse with target cells and virions", Ethnicity & Disease, vol. 18, pp. S214-S219, (Spring 2008).
Simpson, R.J., et al., "Exosomes: proteomic insights and diagnostic potential", Expert Review Proteomics, vol. 6, Issue 3, pp. 267-283, (2009).
Simpson, R.J., et al., "Proteomic profiling of exosomes: current perspectives", Proteomics, vol. 8, pp. 4083-4099, (2008).
Soler-Garcia, A.A., et al., "A urinary biomarker profile for children with HIV-associated renal diseases", Kidney International, vol. 76, pp. 207-214, (2009).
Pisitkun, T., et al., "Identification and proteomic profiling of exosomes in human urine", PNAS, vol. 101, No. 36, pp. 13368-13373, (Sep. 7, 2004).
Booth, A. M., et al., "Exosomes and HIV Gag bud from endosome-like domains of the T cell plasma membrane", the Journal of Cell Biology, vol. 172, pp. 923-935, (2006).
Fang, Y., et al., "Higher-Order Oligomerization Targets Plasma Membrane Proteins and HIV Gag to Exosomes", PLoA Biology, vol. 6, pp. 1267-1283, (2007).
Keller, S., et al., "Exosomes: From biogenesis and secretion to biological function", Immunology Letters, vol. 107, pp. 102-108, (2006).
Pelchen-Matthews, A., et al., "Endosomes, exosomes and Trojan viruses", Trends in Microbiology, vol. 12, pp. 310-316, (2004).
Wyatt, C.M., et al., "HIV-associated Nephropathy in the Era of Antiretroviral Theray", American Journal of Medicine, vol. 120, pp. 488-492, (2007).
Wiley, R.D., et al., "Immature dendritic cell-derived exosomes can mediate HIV-1 trans infection", PNAS, vol. 103, pp. 738-743, (2006).
Yang, X., et al., "Circulating extracellular vesicles as a potential source of new biomarkers of drug-induced liver injury", Toxicology Letters, vol. 225(3), pp. 401-406, (2014).
Conde-Vancells, J., et al., "Isolation of urinary exosomes from animal models to unravel noninvasive disease biomarkers", Chapter 21 from Josic et al. Liver Proteomics: Methods and Protocols, Methods in Molecular Biology, vol. 909, Springer Science and Business Media (2012).
Gonzales, P. et, et al., "Urinary exosomes: is there a future?", Nephrol Dial Transplant, vol. 23, pp. 1799-1801, (2008).
Johnson, P. J., et al., "Structures of disease-specific serum alpha-fetoprotein isoforms", British Journal of Cancer, vol. 83(10), pp. 1330-1337, (2000).
Murugavel, K. G., et al., "Alpha-fetoprotein as a tumor marker in hepatocellular carcinoma: investigations in south Indian subjects with hepatotropic virus and aflatoxin etiologies", International Journal of Infectious Diseases, vol. 12(6), pp. e71-e76, (2008).
Clayton, A., et al., "Adhesion and signaling by B cell-derived exosomes: the role of integrins", The FASEB Journal, vol. 18(9), pp. 977-979, (2004).
Masciopinto, F., et al., "Association of hepatitis C virus envelope proteins with exosomes", European Journal of Immunology, vol. 34, pp. 2834-2842, (2004).
File history of U.S. Appl. No. 12/572,652, filed Oct. 2, 2009.
File history of U.S. Appl. No. 14/159,612, filed Jan. 21, 2014.
File history of U.S. Appl. No. 15/270,848, filed Sep. 20, 2016.
File history of U.S. Appl. No. 15/377,054, filed Dec. 13, 2016.
Novellino et al., "Circulating Hepatitis B Surface Antigen Particles Carry Hepatocellular microRNAs," PLoX One, vol. 7, Issue 3: e31952 (2012).
Sugimachi et al., "Identification of a bona-fide biomarker of micro RNA in serum exosomes to predict recurrence of hepatocellular carcinoma after liver transplantation," Journal of Clinical Oncology, vol. 31, No. 4 Suppl: 183-183 (2013) (abstract only).
El Se rag et al., "Surveillance for hepatocellular carcinoma: in whom and how?" Ther Adv Gastroentrol 4(1 ): 5-10 (2011).
Di Bisceglie, "Hepatitis Band Hepatocellular Carcinoma," Hepatology 49 (5 Suppl.): S56-60 (2009).
U.S. Appl. No. 12/572,652, filed Oct. 2, 2009, Pending.
U.S. Appl. No. 14/159,612, filed Jan. 21, 2014, Patented.
U.S. Appl. No. 15/270,848, filed Sep. 20, 2016, Patented.
U.S. Appl. No. 15/377,054, filed Dec. 13, 2016, Pending.
U.S. Appl. No. 16/601,178, filed Oct. 14, 2019, Pending.

HIVAN (1:10 dilution)
X 60,000

FSGS
X 60,000

AA HIV+
X 60,000

White HIV+
X 60,000

AA HIV negative
X 60,000

SEQUENCE LISTING

```
<160> NUMBER OF SEQ ID NOS: 2

<210> SEQ ID NO 1
<211> LENGTH: 90
<212> TYPE: PRT
<213> ORGANISM: Homo sapiens

<400> SEQUENCE: 1

Ser Tyr Ser Gly Ala Gly Lys Pro Pro Met Phe Gly Asp Tyr Glu Ala
1               5                   10                  15

Gln Arg His Trp Gln Glu Ile Thr Phe Asn Leu Pro Val Lys Gln Trp
            20                  25                  30

Tyr Phe Asn Ser Ser Asp Asn Asn Leu Gln Tyr Trp Gly Leu Asp Tyr
        35                  40                  45

Pro Pro Leu Thr Ala Tyr His Ser Leu Leu Cys Ala Tyr Val Ala Lys
    50                  55                  60

Phe Ile Asn Pro Asp Trp Ile Ala Leu His Thr Ser Arg Gly Tyr Glu
65                  70                  75                  80

Ser Gln Ala His Lys Leu Phe Met Arg Thr
                85                  90

<210> SEQ ID NO 2
<211> LENGTH: 50
<212> TYPE: PRT
<213> ORGANISM: Homo sapiens

<400> SEQUENCE: 2

Gly Asp Tyr Glu Ala Gln Arg His Trp Gln Glu Ile Thr Phe Asn Leu
1               5                   10                  15
```

```
Pro Val Lys Gln Trp Tyr Phe Asn Ser Ser Asp Asn Asn Leu Gln Tyr
                 20                  25                  30

Trp Gly Leu Asp Tyr Pro Pro Leu Thr Ala Tyr His Ser Leu Leu Cys
         35                  40                  45

Ala Tyr
    50
```

EXOSOME-MEDIATED DIAGNOSIS OF HUMAN IMMUNODEFICIENCY VIRUS INFECTION

This application is a continuation application of U.S. patent application Ser. No. 15/377,054, filed on Dec. 13, 2016, which is a continuation application of U.S. patent application Ser. No. 15/270,848, filed on Sep. 20, 2016, now U.S. Pat. No. 10,416,161, which is a continuation application of U.S. patent application Ser. No. 14/159,612, filed on Jan. 21, 2014, now U.S. Pat. No. 9,487,837, which is continuation-in-part application of U.S. patent application Ser. No. 12/572,652, filed Oct. 2, 2009, which claims priority from U.S. Provisional Application Ser. No. 61/102,941, filed Oct. 6, 2008. The entirety of all of the aforementioned applications is incorporated herein by reference.

This application was made with government support under certain grants awarded by the NIH. The government has certain rights in the application.

FIELD

The present application generally relates to methods for diagnosis and, in particular, to methods for diagnosing infections using biomarkers targeting exosomes secreted in bodily fluids.

BACKGROUND

Exosomes are small vesicles 40-100 nm in diameter, that are secreted by a number of different cell types for communicating with other cells via the proteins and ribonucleic acids they carry. An exosome is created intracellularly when a segment of the cell membrane spontaneously invaginates and is endocytosed. The internalized segment is broken into smaller vesicles that are subsequently expelled from the cell. The latter stage occurs when the late endosome, containing many small vesicles, fuses with the cell membrane, triggering the release of the vesicles from the cell. The vesicles (once released are called exosomes) consist of a lipid raft embedded with ligands common to the original cell membrane.

Depending on their cellular origin, exosomes carry uniquely distinct profiles of proteins and/or nucleic acids (such as microRNAs (miRNAs)), which can trigger signaling pathways in other cells and/or transfer exosomal products into other cells by exosomal fusion with cellular plasma membranes. The protein composition of exosomes is distinct from that of other organelles, including early endosomes and plasma membranes, more closely resembling that of late endosomes or multivesicular bodies, (MVBs).

Exosome are released from different cell types in varied physiological contexts. For example, B lymphocytes release exosomes carrying class II major histocompatibility complex molecules, which play a role in antigenic presentation. Similarly, dendritic cells produce exosomes (i.e., dexosomes, Dex), which play a role in immune response mediation, particularly in cytotoxic T lymphocyte stimulation. Some tumor cells secrete specific exosomes (i.e., texosomes, Tex) carrying tumor antigens in a regulated manner, which can present these antigens to antigen presenting cells. Exosomes may also carry pathogen-associated products. For example, exosomes have been known to carry products derived from *Mycobacterium tuberculosis* and *Toxoplasma gondii*-infected cells.

HIV and hepatitis virus infections are often assayed using serum or plasma. The detection of a specific viral antibody is presumptive evidence of a corresponding viral infection, and is typically confirmed by the Western blot procedure. For example, detection of HIV virus by p24 antigen determination or detection of viral RNA by RT-PCR is also used to determine the amount of virus in circulation. CD4/CD8 T cell ratios and other immune function tests are often used to monitor immune status and progression to AIDS. More recently, HIV tests using saliva or epithelia cells in the mouth have also been developed. However, currently there are few tests available to measure viral antigens or antibodies in urine. The detection of HIV and hepatitis proteins in the urine may provide a more rapid method to detect HIV or hepatitis virus infections and/or monitor the progression of disease, particularly viral-associated renal complications.

Hepatitis is an inflammation of the liver, most commonly caused by a viral infection. There are five main hepatitis viruses, referred to as types A, B, C, D and E. Hepatitis A and E are typically caused by ingestion of contaminated food or water. Hepatitis B, C and D usually occur as a result of parenteral contact with infected body fluids (e.g., from blood transfusions or invasive medical procedures using contaminated equipment). Hepatitis B is also transmitted by sexual contact.

Hepatitis A virus (HAV) is an enterically transmitted viral disease that causes fever, malaise, anorexia, nausea, abdominal discomfort and jaundice. HAV is normally acquired by fecal-oral route, by either person-to-person contact, ingestion of contaminated food or water or transmission by pooled plasma products. The absence of a lipid envelope makes HAV very resistant to physicochemical inactivation, and the virus can withstand conventional heat treatment of blood products. The development of sensitive and specific diagnostic assays to identify HAV antigens and/or antibodies in infected individuals as well as nucleic acid-based tests to detect viremic samples to exclude them from transfusion represents an important public health challenge.

Hepatitis B virus (HBV) infects humans and may result in two clinical outcomes. In the majority of clinical infections in adults (90-95%), the virus is cleared after several weeks or months, and the patient develops a lifelong immunity against re-infection. In the remaining cases, however, the virus is not eliminated from the tissues, and the patient remains chronically infected. The sequelae of chronic infection are serious: such individuals are highly likely to develop scarring of the liver tissue (cirrhosis) and may eventually develop hepatocellular carcinoma. HBV is transmitted via infected blood or other body fluids, especially saliva and semen, during delivery, sexual activity, or sharing of needles contaminated by infected blood.

Worldwide, it is estimated that 400 million people are chronically infected with hepatitis B virus (HBV). Chronic hepatitis B (CHB) infection is the most common cause of liver cirrhosis and hepatocellular carcinoma (HCC), with an estimated 500,000-900,000 deaths per year. Continuing HBV replication increases the risk of progression to cirrhosis and HCC.

Hepatitis C virus (HCV) is the causal agent for a largely chronic liver infection originally identified as non-A, non-B hepatitis. HCV has infected about four million people in the United States and 170 million worldwide, about four times as many as HIV and accounts for 90 to 95% of the hepatitis attributable to blood transfusion. It is presumed that the primary route of infection is through contact with contaminated bodily fluids, especially blood, from infected individuals. HCV infection is one of the primary causes of liver transplantation in the United States and other countries. Approximately 40-50% of the liver transplants in the United States are based on HCV infections. The disease frequently progresses to chronic liver damage. While the pathology of HCV infection affects mainly the liver, the virus is found in other cell types in the body including peripheral blood lymphocytes.

The hepatitis delta virus (HDV) is a satellite RNA virus dependent on hepatitis B surface antigens to assemble its envelope and form new virions to propagate infection. HDV has a small 1.7 Kb genome making it the smallest known human virus. However, HDV is the most severe form of viral hepatitis. Compared with other agents of viral hepatitis, acute HDV infection is more often associated with fulminant hepatitis, a rapidly progressive, often fatal form of the disease in which massive amounts of the liver are destroyed. Chronic type D hepatitis is typically characterized by necro-inflammatory lesions, similar to chronic HBV infection, but is more severe, and frequently progresses rapidly to cirrhosis and liver failure, accounting for the disproportionate association of chronic HDV infection with terminal liver disease. Although HDV infection affects fewer individuals than HBV alone, the resulting acute or chronic liver failure is a common indication for liver transplantation in Europe as well as North America. Chronic HDV disease affects 15 million persons worldwide, about 70,000 of whom are in the U.S. The Centers for Disease Control estimates 1,000 deaths annually in the U.S. due to HDV infection.

In view of the wide scope of individuals affected by infectious agents, including various HIV and hepatitis-virus isolates, and the lack of reliable, rapid, cost-effective and less invasive diagnostic tests, there is a need for diagnostic tests for diagnosing infectious agents and infectious disease conditions that is reliable, rapid, cost-effective and less invasive.

SUMMARY

One aspect of the present application relates to a method for diagnosing hepatitis virus infection or a hepatitis disease condition in a subject caused by a hepatitis virus, comprising: (a) preparation of an exosome from a bodily fluid sample from a subject; (b) contacting said exosome preparation with one or more hepatitis virus-associated biomarker binding agent(s) selective for a hepatitis virus and/or with one or more detection reagent(s) suitable for detecting one or more hepatitis virus-associated biomarker(s); and (c) determining whether the exosome preparation comprises at least one hepatitis virus biomarker, wherein a determination of the presence of the at least one hepatitis virus biomarker in step (c) is indicative of hepatitis virus infection or hepatitis disease condition in the subject and wherein a determination of the absence of the at least one hepatitis virus biomarker in step (c) is indicative of the absence of hepatitis virus infection or a hepatitis disease condition in the subject.

In a preferred embodiment, the bodily fluid is urine.

In some embodiments, the exosome preparation comprises whole exosomes. In other embodiments, the exosome preparation comprises an exosome lysate.

In one embodiment, the hepatitis virus is HAV. In another embodiment, the hepatitis virus is HBV. In a further embodiment, the hepatitis virus is HCV. In another embodiment, the hepatitis virus is HDV. In yet another embodiment, the hepatitis virus is HEV.

In certain embodiments, the contacting step (b) further comprises contacting each one of a plurality of exosome preparations with one or more different hepatitis virus biomarker binding agent(s). In certain embodiments, each hepatitis virus biomarker binding agent is selective for a common hepatitis virus. In other embodiments, each hepatitis virus biomarker binding agent is selective for a different hepatitis virus. In certain particular embodiments, the biomarker binding agents are selective for HAV, HBV, HCV, HDV and HEV.

In some embodiments, step (b) comprises contacting the exosome preparation with one or more detection reagents capable of detecting one or more hepatitis virus-associated biomarker(s), whereby the detection reagents are selected from the group consisting of one or more reagents for reverse transcription of RNAs, one or more PCR reagents for amplification and detection of genomic nucleic acids or mRNAs and one or more oligonucleotides for detecting miRNAs.

In certain embodiments, step (b) comprises contacting said exosome preparation with one or more hepatitis virus-associated biomarker binding agent(s) and one or more detection reagent(s) suitable for detecting one or more hepatitis virus-associated biomarkers, wherein the one or more detection reagents are suitable for detecting a miRNA selected from the group consisting of miR-92a, miR-122, miR-148a, miR-194, miR-155, miR-483-5p and miR-671-5p, miR-106b, miR-1274a, miR-130b, miR-140-3p, miR-151-3p, miR-181a, miR-19b, miR-21, miR-24, miR-375, miR-5481, miR-93, and miR-941, miRNA-1, miRNA-122, miR-584, miR-517c, miR-378, miR-520f, miR-142-5p, miR-451, miR-518d, miR-215, miR-376a, miR-133b, miR-367 and combinations thereof.

In other embodiments, step (b) comprises contacting one or more exosome preparation with one or more agents capable of detecting liver damage and/or hepatocellular carcinoma selected from the group consisting of CD10, CD26, CD81, AST, ALT, α-fetoprotein (AFP) and its various isoforms, including AFP-L1, AFP-L2, AFP-L3, AFP-P4, AFP-P5 (E-PHA), and monosialylated AFP; des-carboxy-prothrombin (DCP), α-1-fucosidase (AFU), γ-glutamyl transferase, glypican-3 (GPC-3), squamous cell carcinoma antigen (SCCA), golgi protein 73 (GP73) and mucin 1 (MUC-1), 14-3-3 gamma, alpha-1-fucosidase, gamma-glutamyl transferase, glypican-3, squamous cell carcinoma antigen, protein C (PROC), retinal binding protein 4 (RBP4), alpha-1-B glycoprotein (A1BG), alpha-1-acid glycoprotein (AGP), Mac-2-binding protein (M2BP), complement Factor H (CFH), insulin-like growth factor binding protein acid labeled subunit (IGFALS) and combinations thereof.

The exosome preparation may be prepared by any exosome isolation procedure including differential centrifugation, nanomembrane ultrafiltration, immunoabsorbent capture, size-exclusion chromatography, ultracentrifugation, magnetic activated cell sorting (MACS) and combinations thereof.

In certain embodiments, the diagnosis step is further coupled with the step of administering to the subject a therapeutic drug for hepatitis or the step of obtaining a liver biopsy from the subject for analysis. Any conventional therapeutic drug for hepatitis may be employed.

Another aspect of the present application relates to a method for monitoring the course of a hepatitis virus infection or a hepatitis disease condition in a subject. The method comprises: (a) measuring the level of one or more hepatitis virus-associated biomarkers in a first exosome preparation representing a first time point from a subject; (b) measuring the level of the one or more hepatitis virus-associated biomarkers in a second exosome preparation representing a second time point from a subject; (c) comparing the level of the one or more hepatitis virus-associated biomarkers in the first exosome preparation to the level of the one or more hepatitis virus-associated biomarkers in the second exosome preparation; and (d) determining the disease progression between the first time point and the second time point based on the result of step (c).

Another aspect of the present application relates to a method for monitoring the effectiveness of treatment to a subject with an anti-hepatitis virus agent. The method comprises: (a) determining a hepatitis virus-associated biomarker profile in a first exosome preparation from a subject prior to administration of an anti-hepatitis virus agent; (b) determining a hepatitis virus-associated biomarker profile in a second exosome preparation from said subject after administration of said anti-hepatitis virus agent; (c) comparing the hepatitis virus-associated biomarker profile in the first exosome preparation with the hepatitis virus-associated biomarker profile in the second exosome preparation; and (d) determining the effectiveness of the anti-hepatitis virus agent based on a comparative analysis of the hepatitis virus-associated biomarker profiles in step (c).

Another aspect of the present application relates to a kit for diagnosing hepatitis virus infection and/or a hepatitis disease condition in a subject. The kit comprises: one or more reagents for preparation of an exosome(s); one or more hepatitis virus-associated biomarker binding agents and detection reagents selective for a hepatitis virus, and one or more hepatitis virus-associated biomarker standards.

DETAILED DESCRIPTION

Figure 1:
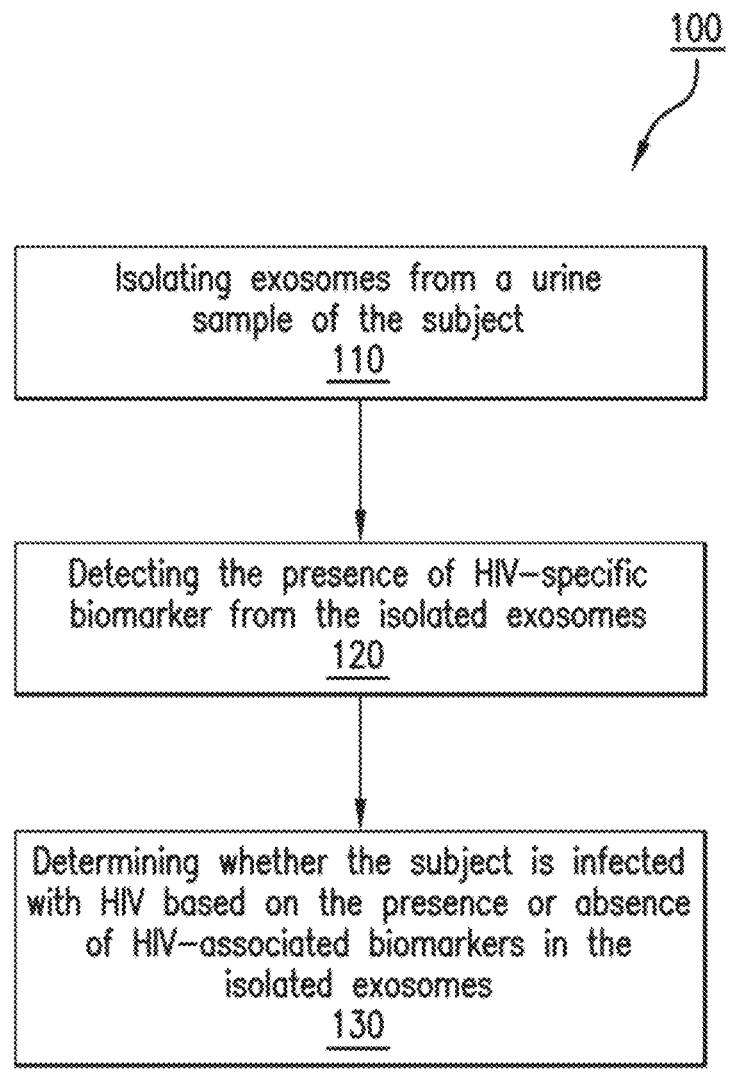
FIG. 1 is a flow chart showing an embodiment of an exemplary method for detecting HIV-infection or monitoring the progress of HIV-infection in a subject using a urine sample from the subject.
Figure 2A:
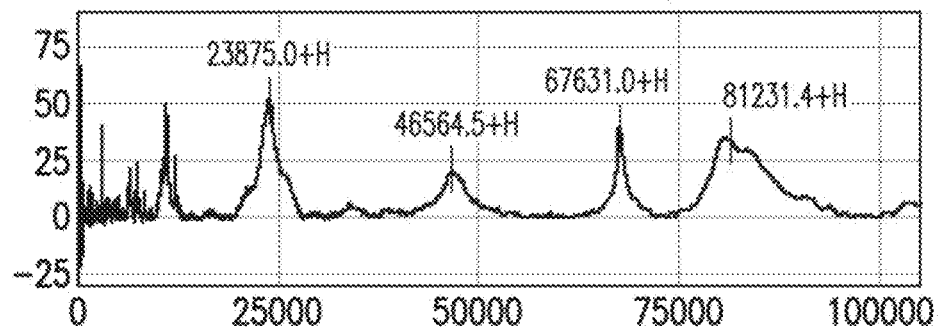
FIGS. 2A-2C are composites of samples SELDI-TOF-MS spectrum of urinary exosomes from patients in the HIVAN groups.
Figure 2B:
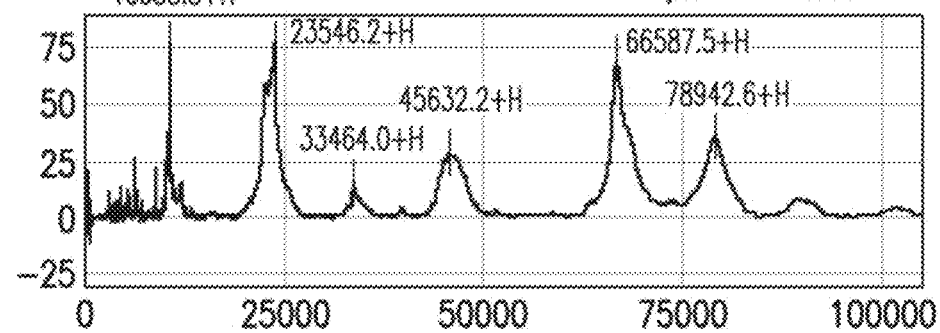
Figure 2C:
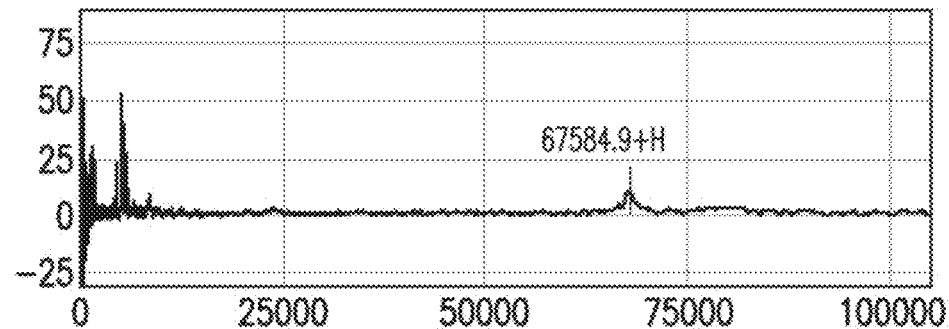
Figure 3A:
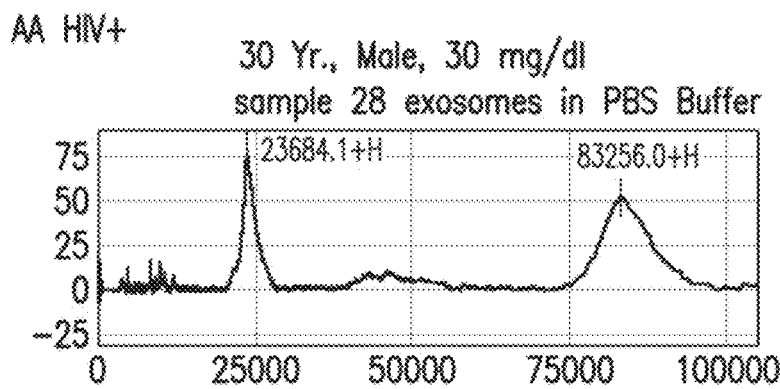
FIGS. 3A-3D are composites of samples SELDI-TOF-MS spectrum of urinary exosomes from patients in the AA HIV+ groups.
Figure 3B:
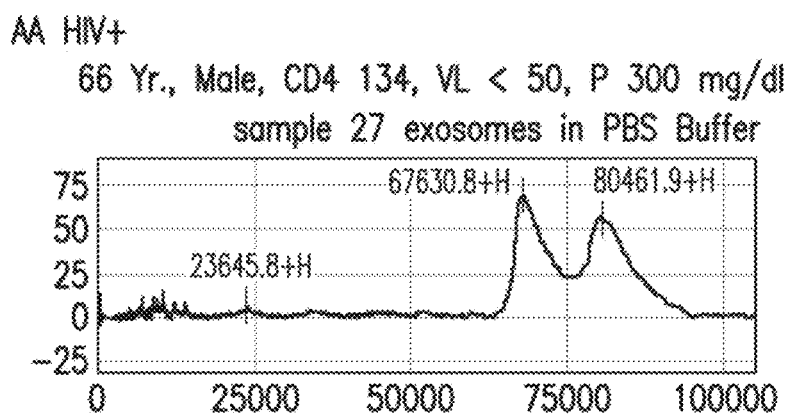
Figure 3C:
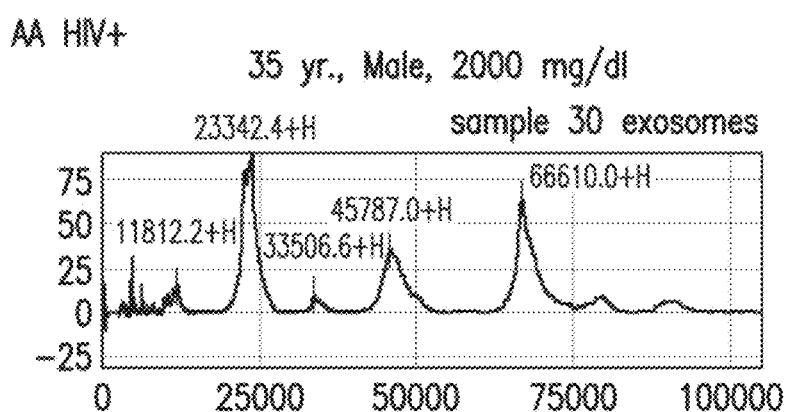
Figure 3D:
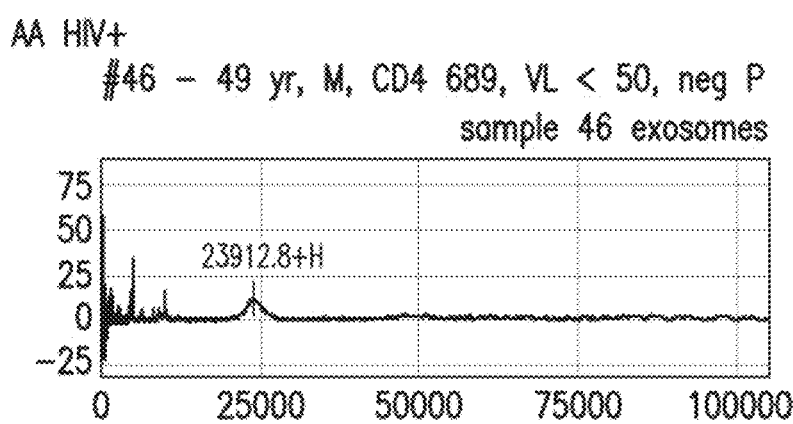
Figure 4A:
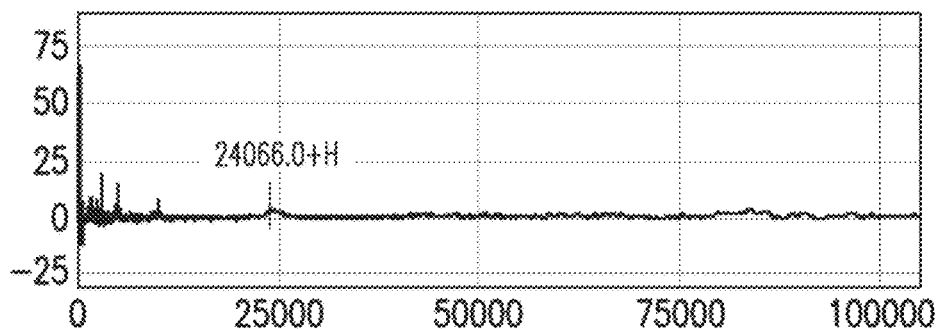
FIGS. 4A-4C are composites of samples SELDI-TOF-MS spectrum of urinary exosomes from patients in the HIV White groups.
Figure 4B:
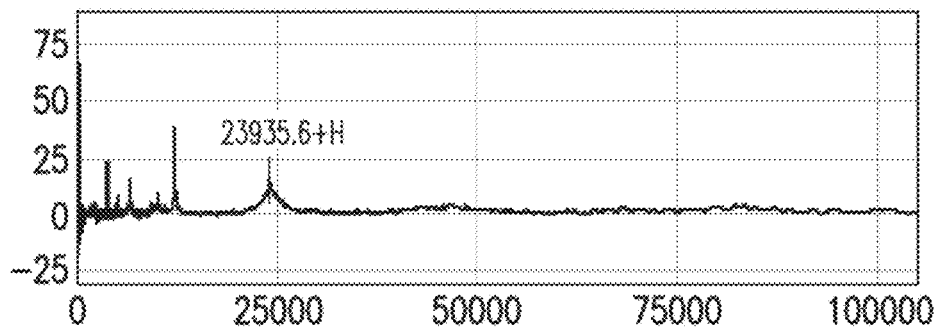
Figure 4C:
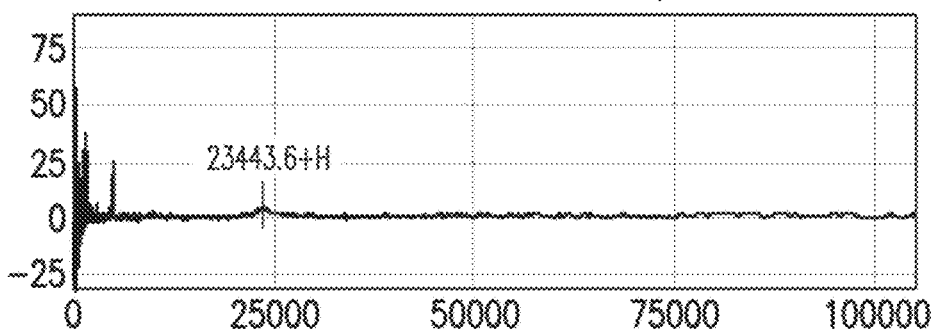
Figure 5A:
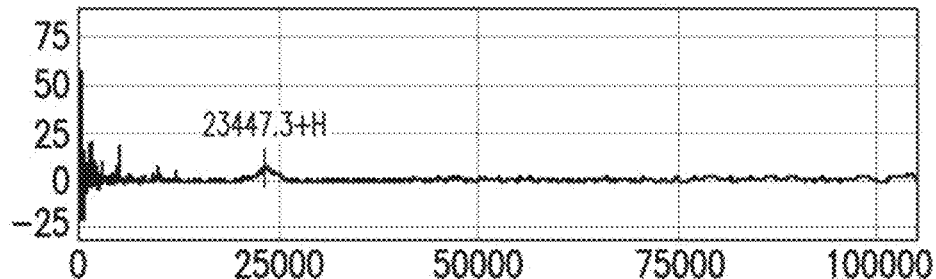
FIGS. 5A-5E are composites of samples SELDI-TOF-MS spectrum of urinary exosomes from patients in the FSGS groups.
Figure 5B:
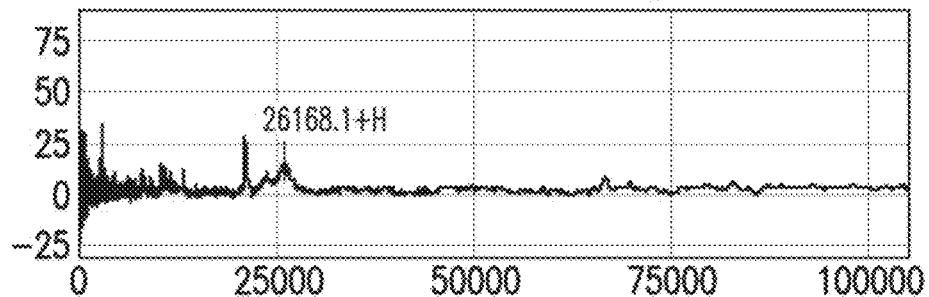
Figure 5C:
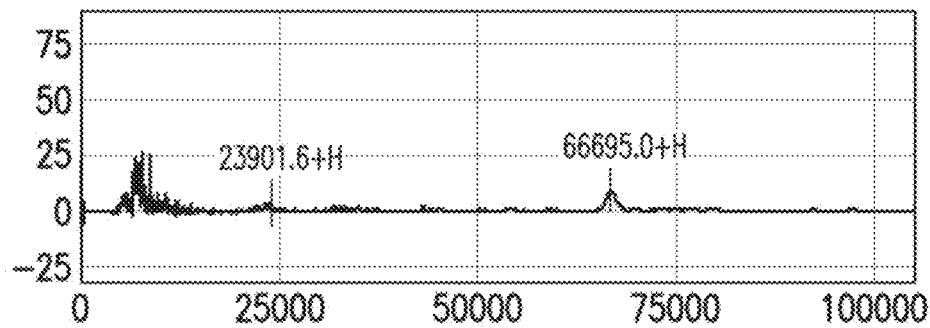
Figure 5D:
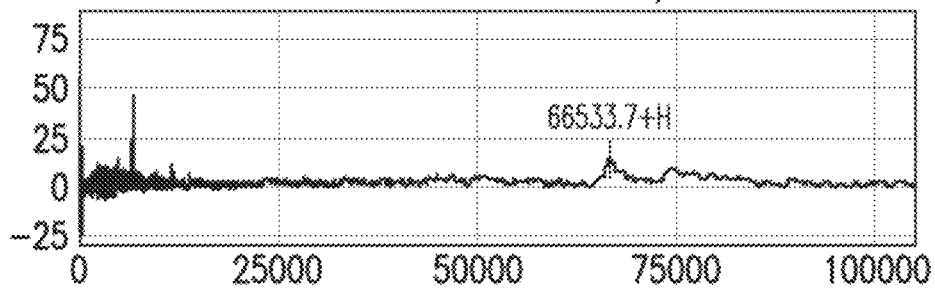
Figure 5E:
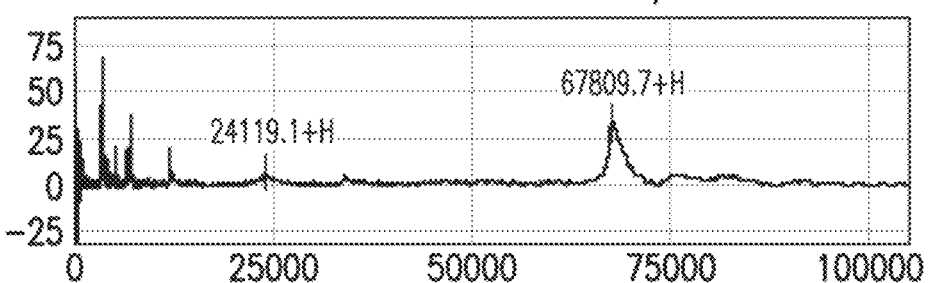
Figure 6A:
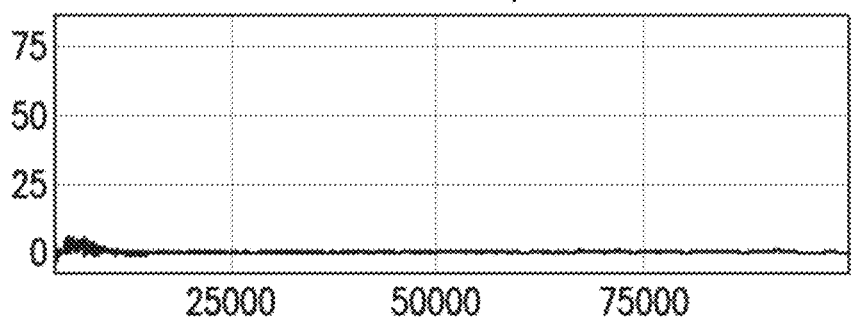
FIGS. 6A-6C are composites of samples SELDI-TOF-MS spectrum of urinary exosomes from patients in the Normal Controls groups.
Figure 6B:
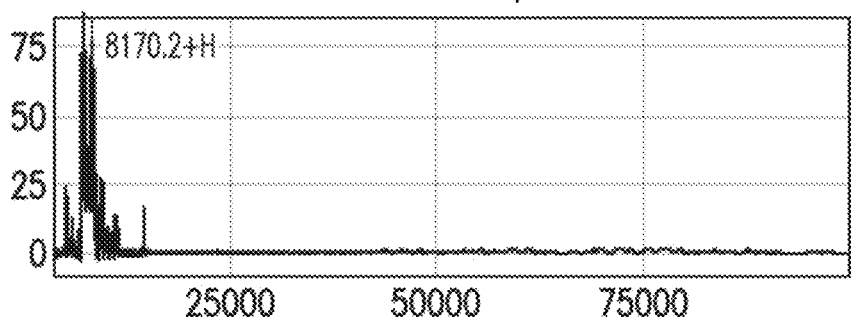
Figure 6C:
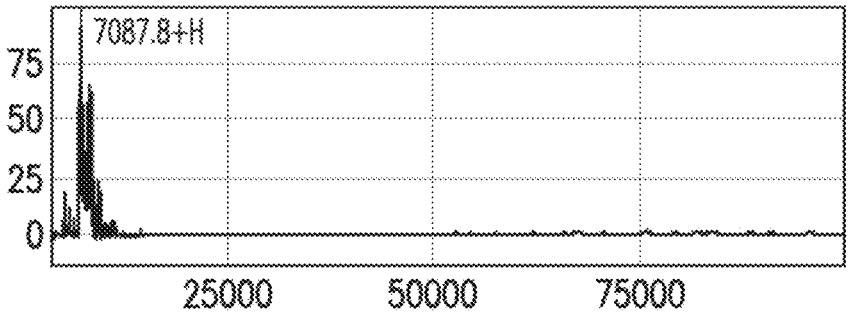
Figure 7A:
FIGS. 7A-7E are composites of transmission electron microscope (TEM) pictures of urinary exosomes isolated from patients from the HIVAN group (Figure A), the FSGS group (Figure B), the African American (AA) HIV+ group (Figure C), the white HIV+ group (Figure D), and the normal control group (Figure E).
Figure 7B:
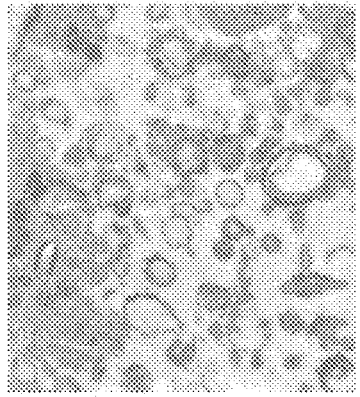
Figure 7C:
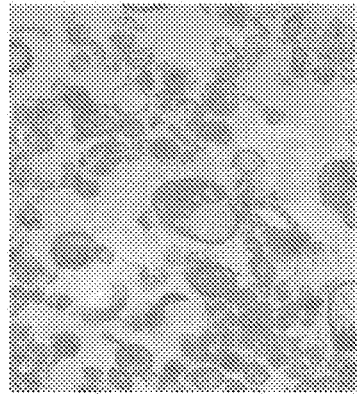
Figure 7D:
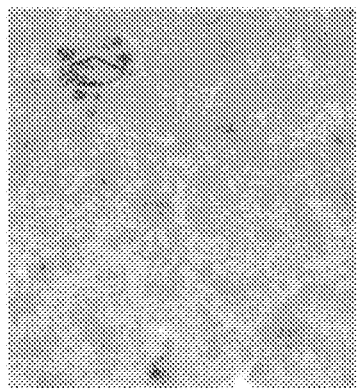
Figure 7E:
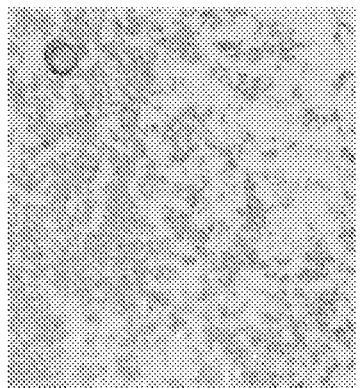

The practice of the embodiments described in further detail below will employ, unless other wise indicated, conventional methods of diagnostics, molecular biology, cell biology, biochemistry and immunology within the skill of the art. Such techniques are explained fully in the literature. All publications, patents and patent applications cited herein, whether supra or infra, are hereby incorporated by reference in their entirety.

It is appreciated that certain features of the invention, which are for clarity described in the context of separate embodiments may also be provided in combination in a single embodiment. Conversely various features of the invention, which are for brevity, described in the context of a single embodiment, may also be provided separately and/or in any suitable sub-combination.

Definitions

As used herein, the following terms shall have the following meanings:

As used herein, the terms "biomarker" and "infectious agent-associated biomarker" are used interchangeably with reference to any molecular entity that can be used as an indicator of an acute infectious disease or chronic infectious disease condition in an organism. The biomarker may be any detectable protein, nucleic acid, such as an mRNA or microRNA, lipid, or any product present and/or differentially expressed in exosomes present in bodily fluids following an infection and/or coincident with an infectious disease condition whose presence and/or concentration reflects the presence, severity, type or progression of an acute or chronic infection in a subject. In molecular terms, biomarkers may be detected and quantitated in a subject using genomics, proteomics technologies or imaging technologies.

An infectious agent-associated biomarker may be viral, bacterial, fungal, protozoan in nature (i.e., encoded by a virus, bacteria, fungus, protozoan etc.) or it may be cellular in nature. Thus, an infectious agent-associated biomarker may be directly derived from the infectious agent, such that the infectious agent encodes for the biomarker. As used herein, the term "virus biomarker" refers to a biomarker directly derived or encoded for by the virus. For example, a hepatitis virus biomarker refers a biomarker directly derived or encoded for by a hepatitis virus. The terms "infectious agent associated cellular biomarker" and "virus-associated cellular biomarker" refer to cellular biomarkers whose expression is altered in response to an infectious agent (such as a virus) or infectious disease condition and whose differential expression relative to non-infected cells is diagnostic of an infection or disease caused by that particular infectious agent.

As used herein, the term "gene product" or "expression product of a gene" refers to the transcriptional products of a gene, such as mRNAs and cDNAs encoded by the gene, and/or the translational products of a gene, such as peptides encoded by the gene, and fragments thereof.

As used herein, the term "infectious disease conditions" refers to conditions that are related to, or resulted from, an infectious disease. As used herein, the term "hepatitis disease conditions" include, but are not limited to, hepatitis, cirrhosis and hepatocellular carcinoma (HCC).

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

One aspect of the present application relates to a method for diagnosing an infection or infectious disease related condition in a subject. The infection may be acute or chronic. In one embodiment, the method comprises the steps of (a) isolating exosomes from a bodily fluid sample of said subject; (b) detecting the presence of one or more infectious agent-associated biomarker(s) from the isolated exosomes; and (c) determining whether the isolated exosomes exhibit a biomarker profile characteristic of an individual who is acutely or chronically infected with a particular infectious agent.

The detecting step may be carried out using any methodology suitable for identifying an infectious agent-associated biomarker, including but not limited to one-dimensional and two-dimensional electrophoretic gel analysis, electrophoresis, Western blot, HPLC, FPLC, ELISA, mass spectrometry (MS), protein sequencing, nucleotide sequencing, PCR, antibody array and combinations thereof.

The determining step may be based on identifying the presence, absence and/or altered expression profiles of one or more infectious agent-associated biomarker(s) in the isolated exosomes obtained from a bodily fluid sample. The determining step may carried out by comparing an infectious agent-associated biomarker profile in a bodily fluid sample (such as urine) to an infectious agent-associated biomarker profile stored in a database. A diagnosis may be based on the results of this comparison.

As used herein, the term "bodily fluid sample" refers to a sample of bodily fluid obtained from a mammal subject, preferably a human subject. Exemplary bodily fluid samples include urine, blood, saliva, serum, plasma, cyst fluid, pleural fluid, ascites fluid, peritoneal fluid, amniotic fluid, epididymal fluid, cerebrospinal fluid, bronchoalveolar lavage fluid, breast milk, tears, sputum, and combinations thereof. In a preferred embodiment, the bodily fluid sample is urine. Unless otherwise noted, as used herein, the terms "bodily fluid sample" and "sample" are to be considered synonymous with any of the above-described bodily fluid samples.

The biomarker profile may consist of one or more biomarkers directly derived from the infectious agent and/or one or more cellular product(s) whose expression profile is characteristic of an individual who is acutely or chronically infected with a particular infectious agent. Accordingly, the step of determining whether the subject carries an infectious agent may be based on detecting the presence, absence or differential expression of one or more infectious agent-associated biomarker(s) present in the isolated exosomes. As used herein, the term "differential expression" refers to a qualitative and/or quantitative changes in biomarker expression levels relative to a control sample.

The term "increased level" refers to an expression level that is higher than a normal or control level customarily defined or used in the relevant art. For example, an increased level of immunostaining of an exosome preparation from a bodily fluid sample is a level of immunostaining that would be considered higher than the level of immunostaining of a control exosome preparation by a person of ordinary skill in the art. As used herein, the described biomarker may exhibit increased expression levels of at least 10%, at least 20%, at least 30%, at least 40%, at least 50%, at least 80%, at least 100%, at least 2-fold, at least 3-fold, at least 5-fold, at least 10-fold, at least 50-fold or at least 100-fold increase or more relative to a suitable reference level.

The term "decreased level" refers to an expression level that is lower than a normal or control level customarily defined or used in the relevant art. As used herein, the described biomarkers may exhibit decreased expression levels of at least at least 10%, at least 20%, at least 30%, at least 40%, at least 50%, at least 80%, at least 100%, at least 2-fold, at least 3-fold, at least 5-fold, at least 10-fold, at least 50-fold or at least 100-fold decrease or more relative to a suitable reference level.

The term "expression level of an infectious agent-associated biomarker" may be measured at the transcription level, in which case the presence and/or the amount of a polynucleotide is determined, or at the translation level, in which case the presence and/or the amount of a polypeptide is determined.

Infectious agent-associated biomarker expression levels may be characterized using any suitable method. Expression levels and expression ratios may be determined at the mRNA level (e.g., by RT-PCR, QT-PCR, oligonucleotide array, etc.) or at the protein level (e.g., by ELISA, Western blot, antibody microarray, etc.). Preferred methodologies for determining mRNA or miRNA expression levels include quantitative reverse transcriptase PCR (QT-PCR), quantitative real-time RT-PCR, oligonucleotide microarray, antibody microarray, or combination thereof. Preferred methodologies for determining protein expression levels include the use of ELISAs and antibody microarrays.

In certain embodiments, an infectious agent-associated biomarker profile may contain from zero to multiple infectious agent-associated biomarkers. Thus, by way of example, an infectious agent-associated profile of a healthy subject may contain no infectious agent-associated biomarkers, whereas infectious agent-associated profile of a patient with an infectious disease may contain a plurality of infectious agent-associated biomarkers. In this method, the genetic background and pertinent information from the medical record of the subject may also be used in the determining step to make a diagnosis.

In another aspect, the method is used to monitor the progression of an infectious disease or infectious disease related condition in the subject based on the presence, absence and/or altered expression profiles of one or more infectious agent-associated biomarker(s) in the isolated exosomes obtained from a bodily fluid sample.

In a related aspect, the method is used to monitor the course of an infectious disease or infectious disease related condition in a subject comprises the steps of (a) measuring the level of one or more biomarkers in exosomes of a first sample obtained from the subject at a first time point; (b) measuring the level of the one or more biomarkers in exosomes of a second sample obtained from the subject at a second time point; (c) comparing the level of the one or more biomarkers at the first time point to the level of the one or more biomarkers at the second time point; and (d) determining the disease progression between the first and the second time point based on the result of step (c).

Another aspect of the present application relates to a method for monitoring the effectiveness of a therapeutic agent in a subject as a function of infectious agent-associated biomarker levels present in the exosomes obtained from a bodily fluid sample. This method includes the steps of: (a) determining an infectious agent-associated biomarker profile in the exosomes of a sample obtained from a subject prior to administration of the therapeutic agent; (b) determining an infectious agent-associated biomarker profile in the exosomes of one or more samples obtained from the subject after administration of the therapeutic agent; (c) comparing the infectious agent-associated biomarker profile in the pre-administration sample with the infectious agent-associated biomarker profile in the post-administration sample(s); and (d) determining the effectiveness of the therapeutic agent based on a comparative analysis of the biomarker profiles in step (c).

In certain embodiments, the method may further contain the step of altering the administration of the agent to the subject. In accordance with this method, the infectious agent-associated biomarker profile may be used as an indicator of the effectiveness of an agent, even in the absence of an observable phenotypic response.

Exemplary mammal subjects for use in accordance with the methods described herein include humans, monkeys, gorillas, baboons, and domesticated animals, such as cows, pigs, horses, rabbits, dogs, cats, goats and the like.

Infectious Agents and Diseases

The infectious agent may be viral, bacterial or fungal in nature. In one embodiment, the infectious agent is human immunodeficiency virus (HIV) type 1 or type 2 (HIV-1 and HIV-2). In another embodiment, the infectious agent is a hepatitis virus selected from the group consisting of hepatitis A virus (HAV), hepatitis B virus (HBV), hepatitis C virus (HCV), hepatitis D virus (HDV) and hepatitis E virus (HEV).

In addition to the HIV and hepatitis viruses, additional viruses include, but are not limited to, human T-cell lymphotropic virus (HTLV) type I and type II (HTLV-I and HTLV-II), parvovirus B19 virus, transfusion transmitted virus (TTV); measles virus; rotaviruses, including Types A, B, C, D, and E; herpesviruses, including Epstein-Barr virus, human cytomegalovirus type 1 (HCMV-1), herpes simplex virus (HSV) types 1 and 2 (HSV-1 and HSV-2), human herpes virus type 6 (HHV-6), human herpes virus type 7 (HHV-7), human herpes virus type 8 (HHV-8); human papilloma virus (HPV) and its many serotypes; influenza type A viruses, including subtypes H1N1 and H5N1; severe acute respiratory syndrome (SARS) coronavirus; and other miscellaneous RNA viruses, including Arenaviridae (e.g., Lassa fever virus (LFV)), Filoviridae (e.g., Ebola virus (EBOV) and Marburg virus (MBGV)); Bunyaviridae (e.g., Rift Valley fever virus (RVFV) and Crimean-Congo hemorrhagic fever virus (CCHFV); and Flaviviridae, including West Nile virus (WNV), Dengue fever virus (DENV), yellow fever virus (YFV), and GB virus C (GBV-C), formerly known as Hepatitis G virus (HGV).

Exemplary bacteria include, but are not limited to Mycobacterium species, including M. tuberculosis; Staphylococcus species, including S. epidermidis, S. aureus, and methicillin-resistant S. aureus; Streptococcus species, including S. pneumoniae, S. pyogenes, S. mutans, S. agalactiae, S. equi, S. canis, S. bovis, S. equinus, S. anginosus, S. sanguis, S. salivarius, S. mitis; other pathogenic Streptococcal species, including Enterococcus species, such as E. faecalis and E. faecium; Haemophilus influenzae, Pseudomonas species, including P. aeruginosa, P. pseudomallei, and P. mallei; Salmonella species, including S. enterocolitis, S. typhimurium, S. enteritidis, S. bongori, and S. choleraesuis; Shigella species, including S. flexneri, S. sonnei, S. dysenteriae, and S. boydii; Brucella species, including B. melitensis, B. suis, B. abortus, and B. pertussis; Neisseria species, including N. meningitidis and N. gonorrhoeae; Escherichia coli, including enterotoxigenic E. coli (ETEC); Vibrio cholerae, Helicobacter pylori, Chlamydia trachomatis, Clostridium difficile, Cryptococcus neoformans, Moraxella species, including M. catarrhalis, Campylobacter species, including C. jejuni; Corynebacterium species, including C. diphtheriae, C. ulcerans, C. pseudotuberculosis, C. pseudodiphtheriticum, C. urealyticum, C. hemolyticum, C. equi; Listeria monocytogenes, Nocardia asteroides, Bacteroides species, Actinomycetes species, Treponema pallidum, Leptospirosa species, Klebsiella pneumoniae; Proteus sp., including Proteus vulgaris; Serratia species, Acinetobacter, Yersinia species, including Y. pestis and Y. pseudotuberculosis; Francisella tularensis, Enterobacter species, Bacteroides species, Legionella species, Borrelia burgdorferi, and the like.

Exemplary fungi include, but are not limited to, Aspergillus species, Dermatophytes, Blastomyces derinatitidis, Candida species, including C. albicans and C. krusei; Malassezia furfur, Exophiala werneckii, Piedraia hortai, Trichosporon beigelii, Pseudallescheria boydii, Madurella grisea, Histoplasma capsulatum, Sporothrix schenckii, Histoplasma capsulatum, Tinea species, including T. versicolor, T. pedis T. unguium, T. cruris, T. capitus, T. corporis, T. barbae; Trichophyton species, including T. rubrum, T. interdigitale, T. tonsurans, T. violaceum, T. yaoundei, T. schoenleinii, T. megninii, T. soudanense, T. equinum, T. erinacei, and T. verrucosum; Mycoplasma genitalia; Microsporum species, including M. audouini, M ferrugineum, M canis, M nanum, M distortum, M gypseum, M fulvum, and the like.

Exemplary protozoans include, but are not limited to Plasmodium falciparum, Cryptosporidium, Isospora belli, Toxoplasma gondii, Trichomonas vaginalis, and Cyclospora species.

An additional infectious agent includes the protease-resistant form of the prion protein (PrP), named scrapie disease associated prion protein (PrP$^{Sc}$), which is associated with a group of fatal neurodegenerative infectious pathologies, including the Creutzfeldt-Jakob disease (CJD), and is known to be associated with exosomes.

In certain embodiments, the infectious disease or infectious disease condition affects the kidney, such as pyelonephritis. In certain preferred embodiments, the infectious disease related condition is HIV-associated nephropathy (HIVAN).

In other embodiments, the infectious disease or infectious disease condition affects the liver, such as hepatitis, cirrhosis and hepatocellular carcinoma (HCC).

Biomarkers

The infectious agent-associated biomarker may be viral, bacterial, fungal or protozoan in nature (i.e., encoded by a virus, bacteria, fungus, protozoan etc.). The infectious agent-associated biomarker may be directly derived from the infectious agent. Alternatively, the infectious agent-associated biomarker may be a cellular biomarker product whose differential expression relative to non-infected cells is diagnostic of an infection or disease caused by that particular infectious agent.

In some embodiments, the biomarker is a protein. In other embodiments, the biomarker is a nucleic acid. Exemplary nucleic acids include both single-stranded and double-stranded polynucleotides or oligonucleotides of DNA or RNA. Exemplary nucleic acids include viral genomic DNAs or RNAs, including reverse transcribed derivatives thereof.

In certain embodiments, viral genomic nucleic acids associated with viral particles (such as hepatitis C virus (HCV)) contained in isolated exosomes may be isolated by conventional RNA or DNA purification methodologies employing e.g., silica gel based spin columns for purification of viral nucleic acids from cell-free body fluids (Qiagen).

In other embodiments, the biomarker is a viral messenger RNA (mRNA), viral microRNA (miRNA) or a viral-induced miRNA. Both mRNAs and miRNAs are known to be shuttled through exosomes. MicroRNAs are small non-coding RNAs responsible of post-transcriptional regulation of gene expression through interaction with messenger RNAs (mRNAs). They are involved in important biological processes and are often dysregulated in a variety of diseases, including cancer and infections. Viruses also encode their own miRNAs, which can be loaded into RNA-induced silencing complexes (RISC) for gene silencing of host's genes and/or their own via blocking mRNA translation and/or initiating mRNA decay. In the past few years evidence of the presence of cellular miRNAs in extracellular human body fluids such as serum, plasma, saliva, and urine has accumulated, including their cofractionation (or colocalization) with exosomes.

Exemplary HIV-1-associated miRNAs include hiv1-mir-H1 and hiv-1-miR-N367.

Exemplary hepatitis-associated miRNAs include miR-122 and mrR-199.

Preferred infectious agent-associated biomarkers include, but are not limited to HIV (e.g., HIV-1, HIV-2)-associated biomarkers and hepatitis virus (e.g., hepatitis A virus (HAV), hepatitis B virus (HBV), hepatitis C virus (HCV), hepatitis D virus (HDV) and hepatitis E virus (HEV))-associated biomarkers. As used herein, the terms "HIV-associated biomarker" or "hepatitis virus-associated biomarker" refer to HIV or hepatitis virus proteins, nucleic acids or fragments thereof, as well as cellular biomarker products whose differential expression relative to non-infected cells is diagnostic of HIV or hepatitis virus infections.

In certain particular embodiments, the biomarker is an HIV-associated protein selected from the group consisting of Nef, gp120, protease, Vif, Gag-Pol, Gag, p24, Rev, reverse transcriptase (RT), Tat, p1, p17, Vpu, Vpr, gp41 and DNA polymerase.

Hepatitis Virus-Associated Biomarkers

In other embodiments the biomarker is a hepatitis virus biomarker associated with hepatitis A virus (HAV), hepatitis B virus (HBV), hepatitis C virus (HCV), hepatitis D virus (HDV) and/or hepatitis E virus (HEV). Any of the hepatitis virus proteins or nucleic acids described herein may be utilized as hepatitis virus biomarkers or hepatitis virus-associated biomarkers in accordance with the present application.

Hepatitis A virus (HAV) is a small, nonenveloped, spherical virus classified in the genus Hepatovirus of the Picornaviridae family. The HAV genome consists of a single-strand, linear, 7.5 kb RNA molecule encoding a polyprotein precursor that is processed to yield the structural proteins and enzymatic activities required for viral replication. HAV encodes four capsid proteins (A, B, C and D) which contain the major antigenic domains recognized by antibodies of infected individuals. In addition to the capsid proteins, antigenic domains have been reported in nonstructural proteins such as 2A and the viral encoded protease. Another important HAV antigenic domain has been described in the junction between the capsid precursor P1 and 2A. In some embodiments, the HAV polyproteins VP0, VP1, and VP3 (aka 1AB, 1D, and 1C, respectively) are used as HAV biomarkers.

Hepatitis B virus is an enveloped non-cytopathic double-stranded circular DNA virus. It is a member of the Hepadnaviridae family. The virus consists of a central core that contains a core antigen (HBcAg) surrounded by an envelope containing a surface protein/surface antigen (HBsAg) and is 42 nm in diameter. It also contains an e antigen (HBeAg) which, along with HBcAg and HBsAg, is helpful in identifying this disease. In HBV virions, the genome is found in an incomplete double-stranded form. Upon infection by HBV, the incomplete partial double stranded DNA is repaired to form a 3.2-kb cccDNA, which serves as a template to transcribe overlapping RNA species including a 3.5-kb pregenomic RNA coding for reverse-transcriptase (polymerase), core, PreS, S and X proteins. These RNAs are then translated into HBV proteins or reverse-transcribed into HBV DNA. All of the HBV proteins play important roles in HBV transcriptional regulation, viral package, reverse-transcription and viral DNA recycling.

Exemplary hepatitis B virus (HBV) biomarker proteins for use in present application include the HBV core antigen (HBcAg), HBV surface antigen (HBsAg), HBV e antigen (HBeAg), HBV X protein (HBx), HBV polymerase, and the HBV envelope proteins S, M, and L.

HCV is an RNA virus of the Flaviviridae, genus Hepacivirus, and is most closely related to the pestiviruses, BVDV and GBV-B. The HCV genome is composed of a single positive strand of RNA, approximately 9.6 kb in length. The HCV genome possesses a continuous, translational open reading frame (ORF) that encodes a polyprotein of about 3,000 amino acids. The structural protein(s) appear to be encoded in approximately the first quarter of the N-terminus region of the ORF, the remainder coding for non-structural proteins. The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Examples of HCV biomarkers include, but are not limited to, HCV core antigen (HCVcAg), HCV C protein, HCV E1 protein, HCV E2 protein, HCV p7 protein, HCV NS2 protein, HCV NS3 protein, HCV NS4a protein, HCV NS4b protein, HCV NS5a protein and HCV NS5b protein.

The hepatitis delta virus (HDV) is a satellite RNA virus dependent on hepatitis B surface antigens to assemble its envelope and form new virions to propagate infection. HDV has a small 1.7 Kb genome making it the smallest known human virus. The HDV virion is composed of a ribonucleoprotein core and an envelope. The core contains HDV-RNA, and hepatitis delta antigen (HDAg), which is the only protein encoded by this virus. The envelope is formed by the surface antigen protein (hepatitis B surface antigen, or HBsAg) of the helper virus, hepatitis B. The envelope is the sole helper function provided by HBV. HDV is able to replicate its RNA within cells in the absence of HBV, but requires HBsAg for packaging and release of HDV virions, as well as for infectivity. As a result of the dependence of HDV on HBV, HDV infects individuals only in association with HBV.

Hepatitis E virus (HEV) is the causative agent of hepatitis E, a form of acute viral hepatitis that is endemic to many resource-limited regions of the world. It is estimated that about 2 billion people, which is about a third of the world population, live in areas endemic for HEV and are at risk for infection. In these areas, hepatitis E is the major form of acute hepatitis; in India for example about 50% of acute hepatitis is due to HEV.

HEV is a small non-enveloped virus with a size of 27-34 nm and is classified as a Hepevirus in the family Hepeviridae. The HEV genome is a single-stranded RNA of ~7.2 kb that is positive-sense, with a 5'-methylguanine cap and a 3' poly(A) stretch, and contains three partially overlapping open reading frames (ORFs)—called orf1, orf2 and orf3. HEV orf1, a polyprotein of 1693 amino acids, encodes the viral nonstructural functions. Functional domains identified in the HEV nonstructural polyprotein include (starting from the N-terminal end)-methyltransferase (MeT), papain-like cysteine protease (PCP), RNA helicase (Hel) and RNA dependent RNA polymerase (RdRp). HEV orf2 encodes a viral capsid protein of 660 amino acids, which is believed to encapsidate the viral RNA genome. HEV orf3 is believed to express a 114 amino acid protein that is dispensable for replication in vitro and is believed to function as a viral accessory protein, likely affecting the host response to infection.

Exemplary hepatitis viral nucleic acid sequences include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., FIELDS VIROLOGY, 2001, supra). Exemplary hepatitis C nucleic acid sequences include, but are not limited to, serine proteases (e.g., NS3/NS4), helicases (e.g., NS3), polymerases (e.g., NS5B), and envelope proteins (e.g., E1, E2, and p7). Hepatitis A nucleic acid sequences are set forth in, e.g., Genbank Accession No. NC_001489; hepatitis B nucleic acid sequences are set forth in, e.g., Genbank Accession No. NC_003977; hepatitis C nucleic acid sequences are set forth in, e.g., Genbank Accession No. NC_004102; hepatitis D nucleic acid sequence are set forth in, e.g., Genbank Accession No. NC_001653; hepatitis E nucleic acid sequences are set forth in, e.g., Genbank Accession No. NC_001434; and hepatitis G nucleic acid sequences are set forth in, e.g., Genbank Accession No. NC_001710.

Cellular Exosomal Biomarkers

Because of their cellular origin, exosomes bear specific protein markers of the endosomal pathway, such as tetraspanins (CD63, CD9 and CD81), heat shock proteins (HSP70) and proteins from the Rab family (e.g., Rab5), Tsg101 and Alix, which are not found in other types of vesicles of similar size. The composition of exosomes is also known to reflect the particular cell types from which they are derived. Accordingly, exosome profiling using cellular exosome markers can provide information correlating the presence of infectious agent biomarkers or infectious agent associated cellular biomarkers with particular cell types in the context of diagnosing a disease. In addition, cellular exosomal surface markers can provide useful targets for affinity purification/detection of exosomes as further described below.

Cellular exosomal markers can provide useful internal controls for determining expression level changes relative to reference samples and can provide useful markers helpful in diagnosing phenotypic tissue changes, including e.g., liver damage, liver fibrosis, inflammation, hepatocellular carcinoma etc. Non-limiting examples of normal exosome marker includes CD9, CD10, CD26, CD53, CD63, CD81, CD82, Rab5, Alix, TSG101, Hsc70 and Hsp90.

In certain embodiments, cellular exosomal markers reflecting tissue damage and/or disease may be exclusively detected in a particular disease state, such as hepatic fibrosis or hepatocellular carcinoma. In other embodiments, the cellular exosomal markers may be increased relative to reference control samples or decreased relative to reference control cells. The increases or decreases may be evident in terms of total expression levels in an exosomal preparation as a whole. Alternatively, the expression level changes may be evident in the total number of exosomes that are positive or negative for a particular marker.

Both types of liver epithelia (i.e., hepatocytes and cholangiocytes), natural killer T (NKT) cells, hepatic stellate cells, adult liver stem cells, and hepatic sinusoidal endothelial cells are exosome-releasing and/or exosome-targeting cells. Exosomal biomarkers associated with hepatic tissues and liver diseases are of particular interest, because their markers can shed light in the incidence of prognosis of hepatitis-related conditions, including hepatocellular carcinoma (HCC).

Like other cell-derived exosomes, hepatic-derived exosomes include typical exosomal markers, which may be utilized in the present application. These include common "marker" proteins, such as tetraspanins (e.g., CD9, CD10, CD26, CD53, CD63, CD81, CD82); endosome-associated proteins that are involved in MVB biogenesis, such as Alix and TSG101; cytoplasmic heat shock proteins, such as Hsc70 and Hsp90; and hepatic cell-type specific proteins and nucleic acids, including mRNAs, microRNAs (miRNAs) and other non-coding RNAs, the composition of which depends on the functional state of the cells (e.g., rested, stimulated, stressed, transformed, etc.)(Masyuk et al., J. Hepatol., 59(3):2013).

Liver Disease Markers

There are a number of markers that may be used individually or in combination for diagnosis of liver diseases, such as hepatitis, hepatic fibrosis and hepatocellular carcinoma. Exemplary liver disease markers include, but are not limited to CD10, CD26, CD81, AST, ALT, α-fetoprotein (AFP) and its various isoforms, including AFP-L1, AFP-L2, AFP-L3, AFP-P4, AFP-P5 (E-PHA), and monosialylated AFP; des-carboxyprothrombin (DCP), α-1-fucosidase (AFU), γ-glutamyl transferase, glypican-3 (GPC-3), squamous cell carcinoma antigen (SCCA), golgi protein 73 (GP73) and mucin 1 (MUC-1), 14-3-3 gamma, alpha-1-fucosidase, gamma-glutamyl transferase, glypican-3, squamous cell carcinoma antigen, protein C (PROC), retinal binding protein 4 (RBP4), alpha-1-B glycoprotein (A1BG), alpha-1-acid glycoprotein (AGP), Mac-2-binding protein (M2BP), complement Factor H (CFH), insulin-like growth factor binding protein acid labeled subunit (IGFALS).

In certain embodiments, an increased level of A1BG or a decreased level of CFH or IGFALS is/are indicative of the incidence and/or severity of acute or chronic hepatitis. In other embodiments, decreasing levels of protein C (PROC) and/or retinal binding protein 4 (RBP4) are indicative of the increasing severity of fibrosis.

miRNA markers for liver disease, such as liver fibrosis include miR-92a, miR-122, miR-148a, miR-194, miR-155, miR-483-5p and miR-671-5p, which exhibit progressive increases at higher fibrotic stages and miR-106b, miR-1274a, miR-130b, miR-140-3p, miR-151-3p, miR-181a, miR-19b, miR-21, miR-24, miR-375, miR-5481, miR-93, and miR-941, which exhibit progressive decreases in expression at higher fibrotic stages.

HCC cell-derived exosomes are known to contain an enriched fraction of small RNAs. Exemplary HCC-associated miRNAs include, but are not limited to miRNA-1, miRNA-122, miR-584, miR-517c, miR-378, miR-520f, miR-142-5p, miR-451, miR-518d, miR-215, miR-376a, miR-133b, miR-367. In certain embodiments, a panel of diagnostic markers includes one or more miRNAs of the miR-17-92 cluster, which are known to be transactivated by c-Myc, such as miR-17-5p, miR-18a, miR-19a, miR-19b, miR-20a and miR-92a-1.

Exosomal biomarkers associated with renal tissues and renal diseases are of particular interest in view of being derived from renal epithelial cells and their ready detection in exosomes isolated from urine. Exemplary exosomal biomarkers from normal urine include apical transporters present in each renal tubule segment, including the proximal tubule (sodium-hydrogen exchanger 3, sodium-glucose co-transporter 1 and 2, and aquaporin-1 (AQP1)), the thick ascending limb (sodium-potassium-chloride co-transporter 2 (NKCC2)), the distal convoluted tubule (thiazide-sensitive Na—Cl co-transporter (NCC)), and connecting tubule/collecting duct (AQP2, rhesus blood group C glycoprotein (RhCG, an ammonia channel), B1 subunit of vacuolar $H^+$-ATPase, and pendrin); hepatocyte growth factor-regulated tyrosine kinase substrate, tumor susceptibility gene 101, vacuolar protein sorting 28 isoform 1, vacuolar protein sorting 28 isoform 2, vacuolar protein sorting 37B, vacuolar protein sorting 37C, EAP25, EAP45, EAP30, CHMP2A, CHMP2B, CHMP3, CHMP4B, CHMP5, CHMP1A, CHMP1B, CHMP6, vacuolar protein sorting factor 4A, and vacuolar protein sorting factor 4B. A database of urinary exosome proteins (and their sequences) from healthy human volunteers based on published and unpublished protein mass spectrometry data from the NHLBI Laboratory of Kidney and Electrolyte Metabolism is publicly available at dir.nhlbi.nih.gov/papers/lkem/exosome/.

Detection of Biomarkers

The step of detecting biomarkers in the exosomes may be carried out using any methodology suitable for isolating and/or detecting an infectious agent-associated biomarker, including but not limited to mass spectrometry (MS), including liquid chromatography-tandem mass spectrometry (LC-MS/MS), surface enhanced laser desorption/ionization time of flight mass spectrometry (SELDI-TOF-MS), high-pressure liquid chromatography-mass spectrometry (HPLC-MS) and fast protein liquid chromatography (FPLC); Fluorescence-activated cell sorter (FACS) analysis, Western blot, enzyme-linked immunosorbent assay (ELISA), including sandwich ELISA, de novo protein sequencing (e.g., via LC-MS/MS), nucleotide sequencing, PCR, quantitative PCR (qPCR) or real-time PCT, RT-PCR, qRT-PCR antibody array, test strips, one-dimensional and two-dimensional electrophoretic gel analysis and combinations thereof.

In certain preferred embodiments, a sample from a subject can be contacted with an antibody that specifically binds an infectious agent-associated biomarker. Optionally, the antibody can be fixed to a solid support to facilitate washing and subsequent isolation of the complex, prior to contacting the antibody with a sample. Examples of solid supports include glass or plastic in the form of a microtiter plate, a stick, a bead, or a microbead. Examples of solid supports encompassed herein include those formed partially or entirely of glass (e.g., controlled pore glass), polysaccharides (e.g., agarose), polyacrylamides, silicones, and plastics such as polystyrene, polypropylene and polyvinyl alcohol. The sample can be diluted with a suitable diluant or eluant before contacting the sample to the antibody.

After incubating the sample with antibodies, the mixture is washed and the antibody-biomarker complex formed can be detected. This can be accomplished by incubating the washed mixture with a detection reagent. This detection reagent may be a second antibody which is labeled with a detectable label, for example. Exemplary detectable labels include magnetic beads (e.g., DYNABEADS™), fluorescent dyes, radiolabels, enzymes (for example, horse radish peroxidase, alkaline phosphatase and others commonly used in an ELISA), and colorimetric labels such as colloidal gold or colored glass or plastic beads. Alternatively, the biomarker in the sample can be detected using an indirect assay, wherein, for example, a second, labeled antibody is used to detect bound biomarker-specific antibody, and/or in a competition or inhibition assay wherein, for example, a monoclonal antibody which binds to a distinct epitope of the marker is incubated simultaneously with the mixture.

Immunoassays can be used to determine presence or absence of infectious agent-associated biomarker(s) in a sample as well as the quantity of the biomarker(s) in the sample. If a marker is present in the sample, it will form an antibody-marker complex with an antibody that specifically binds the marker under suitable incubation conditions described above. The amount of an antibody-marker complex can be determined by comparing to a standard. A standard can be a known compound or another protein known to be present in a sample, for example. As noted above, the test amount of marker need not be measured in absolute units, as long as the unit of measurement can be compared to a control.

The term "antibodies" as used herein includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with an infectious agent-associated biomarker. The antibodies can be tested for their desired activity using the in vitro assays described herein, or by analogous methods, after which their in vivo therapeutic and/or prophylactic activities are tested according to known clinical testing methods.

Exemplary antibody or antibody derived fragments may include any member of the group consisting of: IgG, antibody variable region; isolated CDR region; single chain Fv molecule (scFv) comprising a VH and VL domain linked by a peptide linker allowing for association between the two domains to form an antigen binding site; bispecific scFv dimer; minibody comprising a scFv joined to a CH3 domain; diabody (dAb) fragment; single chain dAb fragment consisting of a VH or a VL domain; Fab fragment consisting of VL, VH, CL and CHI domains; Fab' fragment, which differs from a Fab fragment by the addition of a few residues at the carboxyl terminus of the heavy chain CHI domain, including one or more cysteines from the antibody hinge region; Fab'-SH fragment, a Fab' fragment in which the cysteine residue(s) of the constant domains bear a free thiol group; F(ab')2, bivalent fragment comprising two linked Fab fragments; Fd fragment consisting of VH and CHI domains; derivatives thereof; and any other antibody fragment(s) retaining antigen-binding function. Fv, scFv, or diabody molecules may be stabilized by the incorporation of disulphide bridges linking the VH and VL domains. When using antibody-derived fragments, any or all of the targeting domains therein and/or Fc regions may be "humanized" using methodologies well known to those of skill in the art. In some embodiments, the infectious-agent associated antibody is modified to remove the Fc region.

In certain embodiments, the infectious agent-associated biomarkers are detected using enzyme-linked immunosorbent assay (ELISA) which is typically carried out using antibody coated assay plate or wells. Commonly used ELISA assay employs either a sandwich immunoassay or a competitive binding immunoassay.

A sandwich ELISA may be used to capture, detect, characterize and quantify exosomes from small volumes of body fluids. A sandwich ELISA employs two antibodies, which bind to different sites on the antigen or ligand. The primary antibody, which is highly specific for the antigen, is attached to a solid surface. The antigen is then added followed by addition of a second antibody referred to as the detection antibody. The detection antibody binds the antigen to a different epitope than the primary antibody. Each of these antibodies may be directed to a different exosomal marker epitope on the same or different exosomal proteins, whereby the primary antibody captures the exosome or protein therefrom via the first exosomal protein and the detection antibody facilitates quantitation of a exosomal protein bound thereto. As a result, the exosome or protein therefrom is "sandwiched" between the two antibodies. A sandwich ELISA may also use lectins to capture exosomes. Lectins have a particular affinity for glycan markers, such as glycoproteins, which are often present in tumor cell-derived exosomes, such as HCC-derived exosomes.

Non-limiting examples of lectins for immobilization on a substrate include Lens culinaris agglutin (LCA), Galanthus nivalis lectin (GNA), Narcissus pseudonarcissus lectin (NPL), Allium sativum lectin (ASA), Lens culinaris lectin (LCH), Sambucus nigra lectin (SNA), Maackia amurensis lectin (MAL), Concanavalin A (Con A), Aleuria aurantia lectin (AAL), Lotus tetragonolobus lectin (LTL), Naja mossambica lectin (NML), Dolichos biflorus agglutinin (DBA), Helix aspersa lectin (HAL), Psophocarpus tetragonolobus lectin II (PTL II), Wisteria floribunda lectin (WFL), Erythrina cristagalli lectin (ECL), Griffonia simplicifolia lectin II (GSL II) and Phaseolus vulgaris leucoagglutinin (PHA-L).

AFP-L3, an isoform of alpha-fetoprotein, is the major glycoform in the serum of HCC patients and is known to bind LCA. For diagnosis of HCC, the AFP-L3 marker may be detected in combination with other AFP glycoforms, including AFP-P4, AFP-P5 (E-PHA), and monosialylated AFP. In contrast, the L1 isoform of AFP (AFP-L1) may be used to diagnose a non-HCC inflammation of liver disease condition. In certain preferred embodiments, LCA lectin is used to bind exosomes in bodily fluids from HCC subjects.

The binding affinity for the antigen (via antibodies or lectins) is usually the main determinant of immunoassay sensitivity. As the antigen concentration increases the amount of binding agent bound increases leading to a higher measured response. The standard curve of a sandwich-binding assay has a positive slope. To quantify the extent of binding different reporters can be used. Typically an enzyme is attached to the secondary antibody which must be generated in a different species than primary antibodies (i.e., if the primary antibody is a rabbit antibody than the secondary antibody would be an anti-rabbit from goat, chicken, etc., but not rabbit). The substrate for the enzyme is added to the reaction that forms a colorimetric readout as the detection signal. The signal generated is proportional to the amount of target antigen present in the sample. The antibody linked reporter used to measure the binding event determines the detection mode. A spectrophotometric plate reader may be used for colorimetric detection. Several types of reporters have been developed in order to increase sensitivity in an immunoassay. For example, chemiluminescent substrates have been developed which further amplify the signal and can be read on a luminescent plate reader. Also, a fluorescent readout may be obtained where the enzyme step of the assay is replaced with a fluorophor tagged antibody. This readout is then measured using a fluorescent plate reader.

Biomarker Panels

In certain embodiments, a biomarker panel of at least 2, 3, 4, 5, 10, 15, 20, 25, 30, 40 or 50 liver disease markers in microarray may be employed. In certain embodiments, a biomarker panel assays expression of biomarker proteins. In other embodiments, the biomarker panel assays expression of biomarker mRNAs or miRNAs. For example, infectious agent-associated biomarkers may be detected using a biomarker microarray panel containing immobilized infectious agent-associated biomarker-specific antibodies on a substrate surface. The microarray can be used in a "sandwich" assay in which the antibody on the microarray captures an infectious agent-associated biomarker in the test sample and the captured marker is detected by a labeled secondary antibody that specifically binds to the captured marker. In a preferred embodiment, the secondary antibody is biotinylated or enzyme-labeled. The detection is achieved by subsequent incubation with a streptavidin-fluorophore conjugate (for fluorescence detection) or an enzyme substrate (for colorimetric detection).

Typically, a microarray assay contains multiple incubation steps, including incubation with the samples and incubation with various reagents (e.g., primary antibodies, secondary antibodies, reporting reagents, etc.). Repeated washes are also needed between the incubation steps. In one embodiment, the microarray assays is performed in a fast assay mode that requires only one or two incubations. It is also conceivable that the formation of a detectable immune complex (e.g., a captured infectious agent-associated biomarker/anti-marker antibody/label complex) may be achieved in a single incubation step by exposing the biomarker microarray to a mixture of the sample and all the necessary reagents. In one embodiment, the primary and secondary antibodies are the same antibody.

In another embodiment, the biomarker microarray provides a competitive immunoassay. Briefly, a microarray comprising immobilized anti-marker antibodies is incubated with a test sample in the presence of a labeled infectious agent-associated biomarker standard. The labeled infectious agent-associated biomarker competes with the unlabeled infectious agent-associated biomarker in the test sample for the binding to the immobilized antigen-specific antibody. In such a competitive setting, an increased concentration of the specific infectious agent-associated biomarker in the test sample would lead to a decreased binding of the labeled infectious agent-associated biomarker standard to the immobilized antibody and hence a reduced signal intensity from the label.

In certain embodiments, a diagnosis may include an oligonucleotide microarray for detecting and quantitating miRNA expression level(s). An oligonucleotide microarray consists of an arrayed series of a plurality of microscopic spots of oligonucleotides, called features, each containing a small amount (typically in the range of picomoles) of a specific oligonucleotide sequence. The specific oligonucleotide sequence can be a short section of a gene or other oligonucleotide element that is used as a probe to hybridize a cDNA or cRNA sample under high-stringency conditions. Probe-target hybridization is usually detected and quantified by fluorescence-based detection of fluorophore-labeled targets to determine relative abundance of nucleic acid sequences in the target. The oligonucleotide probes are typically attached to a solid surface by a covalent bond to a chemical matrix (via epoxy-silane, amino-silane, lysine, polyacrylamide or others). The solid surface can be glass or a silicon chip or microscopic beads. Oligonucleotide arrays are different from other types of microarray only in that they either measure nucleotides or use oligonucleotide as part of its detection system.

A biomarker microarray panel can be processed in manual, semi-automatic or automatic modes. Manual mode refers to manual operations for all assay steps including reagent and sample delivery onto microarrays, sample incubation and microarray washing. Semi-automatic modes refer to manual operation for sample and reagent delivery onto microarray, while incubation and washing steps operate automatically. In an automatic mode, three steps (sample/reagent delivery, incubation and washing) can be controlled by a computer or an integrated breadboard unit with a keypad. For example, the microarray can be processed with a PROTEINARRAY™ Workstation (PerkinElmer Life Sciences, Boston, Mass.) or Assay 1200™. Workstation (Zyomyx, Hayward, Calif.). Scanners by fluorescence, colorimetric and chemiluminescence, can be used to detect microarray signals and capture microarray images. Quantitation of microarray-based assays can also be achieved by other means, such as mass spectrometry and surface plasma resonance. Captured microarray images can be analyzed by stand-alone image analysis software or with image acquisition and analysis software package. For example, quantification of an antigen microarray can be achieved with a fluorescent PMT-based scanner—SCANARRAY™ 3000 (General Scanning, Watertown, Mass.) or colorimetric CCD-based scanner—VisionSpot (Allied Biotech, Ijamsville, Md.). Typically, the image analysis would include data acquisition and preparation of assay report with separate software packages. To speed up the whole assay process from capturing an image to generating an assay report, all the analytical steps including image capture, image analysis, and report generation, can be confined in and/or controlled by one software package. Such an unified control system would provide the image analysis and the generation of assay report in a user-friendly manner.

Exosomes may be isolated by a variety of methodologies, including but not limited to density gradient centrifugation, differential centrifugation, nanomembrane ultrafiltration, immunoabsorbent capture, affinity capture, size-exclusion chromatography, ultracentrifugation, and ultracentrifugation followed by size-exclusion chromatography (UC-SEC), magnetic activated cell sorting (MACS), combination thereof, and the like.

In one embodiment, the isolating step is accomplished by sedimenting exosomes in a bodily fluid sample via centrifugation. The sedimented exosomes are washed and resuspended at a proper concentration for further analysis. In certain embodiments, the sample may be centrifuged at 100,000×g or above for 10-120 or 60-120 minutes to sediment the exosomes.

In certain embodiments, the exosomes in the bodily fluid sample are precipitated by a two-step centrifugation process that includes a low g force centrifugation to remove calls and other large particles in the urine and a high g force centrifugation to precipitate the exosomes. In one embodiment, the sample is first centrifuged at 5,000-25,000×g for 5-30 minutes. The supernatant is then transferred to another tube and is centrifuged again at 100,000×g or above for 30-120 minutes to sediment the exosomes. In a preferred embodiment, the bodily fluid sample is first centrifuged at 20,000-22,000×g for 10-20 minutes. The supernatant is then transferred to another tube and is centrifuged again at 100,000×g for 30-90 minutes to sediment the exosomes. The sedimented exosomes are then resuspended in a liquid medium for further analysis.

The liquid medium can be isotonic, hypotonic, or hypertonic. In certain embodiments, the liquid medium contains a buffer and/or at least one salt or a combination of salts. Buffers can maintain pH within a particular range, for example, between 1 and 12, and are also referred to as pH stabilizing agents. More typically, pH will range within about pH 5.0 to about pH 12.0. A particular example of a pH stabilizing agent is a zwitterion. Specific non-limiting examples of pH stabilizing agents include Tris(hydroxymethyl)aminomethane hydrochloride (TRIS), N-(2-hydroxyethyl)piperazine-N'-2-ethanesulfonic acid (HEPES), 3-(N-morpholino) propanesulfonic acid (MOPS), 2-(N-morpholino) ethanesulfonic acid (IVIES), N-tris[hydroxymethyl]methyl-2-aminoethanesulfonic acid (TES), N-[carboxymethyl]-2-aminoethanesulfonic acid (ACES), N-[2-acetamido]-2-iminodiacetic acid (ADA), N,N-bis[2-hydroxyethyl]-2-aminoethanesulfonic acid (BES), N-[2-hydroxyethyl]piperazine-N-[2-hydroxypropoanesulfonic acid] (HEPPSO), N-tris[hydroxymethyl]methylglycine (TRICINE), N,N-bis[2-hydroxyethyl]glycine (BICINE), 4-(cyclohexylamino)-1-butanesulfonic acid (CABS), 3-(cyclohexylamino)-1-propanesulfonic acid (CAPS), 3-(cyclohexylamino-2-hydroxy-1-propanesulfonic acid (CAPSO), 2-(cyclohexylamino)ethanesulfonic acid (CHES), N-(2-hydroxyethyl)piperazine-N'-(3-propanesulfonic acid) (EPPS), piperazine-N,N'-bis(2-ethanesulfonic acid (PIPES), [(2-hydroxy-1,1-bis[hydroxymethyl]ethyl) amino]-1-propanesulfonic acid (TAPS), N-tris(hydroxymethyl)methyl-4-aminobutane sulfonic acid (TABS), 2-amino-2-methyl-1-propanol (AMP), 3-[(1,1-dimethyl-2-hydroxyethyl)amino]-2-hydroxypropanesulfonic acid (AMPSO), ethanolamine and 3-amino-1-propanesulfonic acid. Additional specific non-limiting examples of pH stabilizing agents include potassium chloride, citric acid, potassium hydrogenphthalate, boric acid, potassium dihydrogenphosphate, diethanolamine, sodium citrate, sodium dihydrogenphosphate, sodium acetate, sodium carbonate, sodium tetraborate, cacodylic acid, imidazole, 2-Amino-2-methyl-1-propanediol, tricine, Gly-Gly, bicine, and a phosphate buffer (e.g., sodium phosphate or sodium-potassium phosphate, among others).

Buffers or pH stabilizing agents are typically used in a range of about 0.1 mM to about 500 mM, in a range of about 0.5 mM to about 100 mM, in a range of about 0.5 mM to about 50 mM, in a range of about 1 mM to about 25 mM, or in a range of about 1 mM to about 10 mM. More particularly, buffers can have a concentration of about (i.e., within 10% of) 1 mM, 2 mM, 5 mM, 10 mM, 15 mM, 20 mM, 25 mM, 30 mM, 40 mM, or 50 mM.

The liquid medium may further contain a chelating agent. Chelating agents typically form multiple bonds with metal ions, and are multidentate ligands that can sequester metals. Metal sequestration can in turn reduce or prevent microbial growth or degradation of biomolecules (e.g., peptide or nucleic acid), which in turn can improve preservation of biomolecules absorbed to a substrate. Specific non-limiting examples of chelating agents include EDTA (ethylenediamine-tetraacetic acid), EGTA (ethyleneglycol-O,O'-bis(2-aminoethyl)-N,N,N',N'-tetraacetic acid), GEDTA (glycoletherdiaminetetraacetic acid), HEDTA (N-(2-hydroxyethyl) ethylenediamine-N,N',N'-triacetic acid), NTA (nitrilotriacetic acid), salicylic acid, triethanolamine and porphine. Typical concentrations of chelating agents are in a range of about 0.1 mM to about 100 mM, in a range of about 0.5 mM to about 50 mM, or in a range of about 1 mM to about 10 mM.

The liquid medium may also contain a denaturing agent. Denaturing agents and detergents typically form a chemical bridge between hydrophobic and hydrophilic environments, which in turn disrupt or diminish the hydrophobic forces required to maintain native protein structure. Particular non-limiting chemical classes of denaturing agents and detergents include anionic surfactants, nonionic surfactants, cationic surfactants and ampholytic surfactants. Specific non-limiting examples of detergents include guanidinium thiocyanate, sodium dodecyl sulfate, sodium lauryl sulfate, NP40, Triton X-100, Tween, sodium cholate, sodium deoxycholate, benzethonium chloride, CTAB (cetyltrimethylammonium bromide), hexadecyltrimethylammonium bromide, and N,N-dimethyldecylamine-N-oxide.

The liquid medium may further contain a denaturing agent. Reducing agents and antioxidants typically inhibit microbial growth and reduce biomolecule oxidation. Particular non-limiting classes of such agents include free radical scavenging agents. Specific non-limiting examples of reducing agents and anti-oxidants include DTT (dithiothreitol), dithioerythritol, urea, uric acid, 2-mercaptoethanol, cysteine, vitamin E, vitamin C, dithionite, thioglycolic acid and pyrosulfite.

The liquid medium may further contain a preservative or stabilizing agent. Preservatives or stabilizing agents can be used if it is desired to inhibit or delay degradation of an the biomarkers of interest. Specific non-limiting examples of preservatives and stabilizing agents include sodium azide and polyethylene glycol (PEG). Typical concentrations of preservatives and stabilizing agents range from about 0.05% to about 1%.

The liquid medium may further contain one or more protease inhibitors. Protease inhibitors inhibit peptide degradation. Particular non-limiting classes of protease inhibitors include reversible or irreversible inhibitors of substrate (e.g., peptide) binding to the protease. Particular non-limiting classes of protease inhibitors include serine and cysteine protease inhibitors. Specific non-limiting examples of protease inhibitors include PMSF, PMSF Plus, APMSF, antithrombin III, amastatin, antipain, aprotinin, bestatin, benzamidine, chymostatin, calpain inhibitor I and II, E-64,3,4-dichloroisocoumarin, DFP, elastatinal, leupeptin, pepstatin, 1,10-phenanthroline, phosphoramidon, TIMP-2, TLCK, TPCK, trypsin inhibitor (soybean or chicken egg white), hirustasin, alpha-2-macroglobulin, 4-(2-aminoethyl)-benzenesulfonyl fluoride hydrochloride (AEB SF) and Kunitz-type protease inhibitors.

In another embodiment, exosomes in a bodily fluid sample are collected by passing the bodily fluid sample through a filter having a pore size that is smaller than the average size of exosomes. The exosomes are then removed from the filter and resuspended at a proper concentration for further analysis. In certain embodiments, exosomes in the bodily fluid samples are collected using centrifuge filters with a molecular weight cutoff of 500 kd-50 kd. In one embodiment, exosomes in the bodily fluid samples are collected using centrifuge filters with a molecular weight cutoff of 100 kd.

In other embodiments, bodily fluids or cell-free supernatants thereof may be incubated with beads coated with one or more antibodies recognizing marker proteins on the surface of exosome particles. Exemplary exosome surface markers include, but are not limited to MEW class II markers, including those of the HLA DP, DQ and DR haplotypes; CD9, CD63, CD81 and CD82.

For example, exosome surface marker-directed antibodies be attached to magnetic beads, such as those manufactured by DYNABEADS® (Dynal, Oslo, Norway) for affinity purification of exosomes. More specifically, exosomes having CD63 on their surface may be isolated using antibody coated magnetic bead particles. DYNABEADS® are superparamagnetic polystyrene beads which may be conjugated with anti-human CD63 antibody, either directly to the bead surface or via a secondary linker (e.g., anti-mouse IgG). The beads may be between 1 and 4.5 µm in diameter.

Antibody coated DYNABEADS® may be added to an exosome sample prepared using a volume-excluding polymer and incubated at 2-8° C. or at room temperature from 5 minutes to overnight. DYNABEADS® with bound exosomes may then be collected using a magnet. The isolated bead-bound exosomes may then be resuspended in an appropriate buffer, such as phosphate buffered saline, and used for downstream analysis (qRT-PCR, sequencing, Westerns, flow cytometry, etc.). Similar protocols may be used for any other exosome surface marker for which an antibody or other specific ligand is available. Indirect binding methods such as those using biotin-avidin may also be used.

Once an isolated exosome sample has been prepared, the contents of the exosome may be analyzed directly or further extracted for additional study and characterization. Biological material which may be extracted from exosomes includes proteins, peptides, RNA and DNA, lipids. For example, the MIRVANA' PARIS' Kit (AM1556, Life Technologies) may be used to recover native protein and RNA from exosomes samples, including small RNAs, such as miRNAs, snRNAs, and snoRNAs.

Total RNA may be extracted using acid-phenol chloroform extraction. RNA may then be purified using a glass-fiber filter under conditions that recover small-RNA containing total RNA, or that separate small RNA species less than 200 nucleotides in length from longer RNA species such as mRNA. Because the RNA is eluted in a small volume, no alcohol precipitation step may be required for isolation of the RNA.

Kits

Another aspect of the present application relates to a kit for diagnosing an infectious agent-associated disease or monitoring the progress of an infectious agent-associated disease in a subject. The kit contains one or more reagents for preparing an exosome preparation; one or more infectious agent-associated biomarker binding agents selective for one or more infectious disease(s) or infectious disease condition(s); one or more infectious agent-associated biomarker standard(s), and one or more detection reagents for detecting binding of the one or more biomarker binding agents(s) to one or more infectious agent-associated biomarker(s).

The detection reagents for detecting binding of the one or more biomarker binding agents(s) to one or more infectious agent-associated biomarker(s) may include antibody reagents, including horseradish peroxidase (HRP)-antibody conjugates and the like for detection and quantitation of protein levels, as well amplification primers or oligonucleotide probes for detection and quantitation of infectious agent associated genomic nucleic acids, mRNA levels and miRNAs.

In some embodiments, the kit is a hepatitis virus infection detection kit comprising one or more reagents for preparing an exosome preparation; one or more hepatitis virus-associated biomarker binding agents; one or more hepatitis virus-associated biomarker standards, and one or more detection reagents for detecting binding of the one or more hepatitis virus-associated biomarker binding agents to one or more hepatitis virus-associated biomarkers. In a related embodiment, the one or more hepatitis virus-associated biomarker binding agents bind to one or more hepatitis virus biomarkers selected from the group consisting of Hep C core antigen, Hep C NS2 protein, Hep C NS3 protein and Hep C NS4 protein.

In certain embodiments, the kit comprises one or more centrifuge filters for collecting exosomes in the bodily fluid samples. In a related embodiment, the one or more centrifuge filters have a molecular weight cutoff of 500 kd-50 kd. In another related embodiment, the one or more centrifuge filters have a molecular weight cutoff of 100 kd.

The kits described above may additionally include liquids suitable for resuspending exosomes isolated from a bodily fluid sample and one or more container(s) for collecting a bodily fluid sample and/or a centrifuge filter for isolating exosomes from the bodily fluid sample. Additionally, the kits described above will typically include a label or packaging insert including a description of the components or instructions for use. Exemplary instructions include, instructions for collecting a bodily fluid sample, for harvesting exosomes from the sample, and for detecting an infectious agent-associated biomarker.

The present application is further illustrated by the following examples which should not be construed as limiting. The contents of all references, patents and published patent applications cited throughout this application, as well as the Figures and Tables, are incorporated herein by reference.

EXAMPLE 1: MATERIALS AND METHODS

Patients

HIV+ patients, at various stages of disease, were recruited for this study from four clinical sites in the Atlanta metropolitan area. Only those patients on dialysis were excluded from this study. All samples were collected in accordance with protocols approved by the Institutional Review Board and the Human Subjects Research Committee at Morehouse School of Medicine, and informed consent was obtained from all patients and healthy volunteers according to the guidelines instituted by the Institutional Review Board. Patients were divided into five groups: African American patients with HIV (AA HIV+), white patients with HIV (White HIV+), patients with HIVAN (HIVAN), African American patients with no HIV but FSGS, and healthy controls. Pertinent information was also collected from the medical record of the patients.

Sample Collection and Storage

Urine samples were collected from patients during routine clinical visits. Clinical data were obtained from the medical record of the patients. Urine was collected in sterile containers and transported back to the laboratory. Urinalysis was performed on each specimen using a MULTISTIX® 10 SG Reagent Strip (Bayer Corporation, Elkhart, Ind.) and the albumin to creatine ratio determined by a Siemens CLINITEK® Microalbumin dipstick (Bayer Corp.). The strips were read on a Siemens CLINITEK STATUS® instrument (Bayer Corp.). Samples were centrifuged at 2,000×g for 10 minutes to remove whole cells and sediment. The remaining urine samples were aliquoted into 4 ml volumes and stored at −80° C. until they were analyzed.

Isolation of Exosomes

Two methods were evaluated for the isolation of exosomes, either high speed ultracentrifugation or ultrafiltration using a molecular weight cutoff filter. For the ultracentrifugation method, 4 ml of urine were transferred into a polycarbonate centrifuge tube and centrifuged at 21,000×g for 15 minutes. The supernatant was removed and again centrifuged at 100,000×g for 60 minutes to sediment the exosomes. The excess urine was decanted and the pellet was reconstituted in 100 μl phosphate buffered saline (PBS) and stored at 4° C. For the ultrafiltration method, 4 ml of urine were added to an AMICON ® Ultra centrifugal filter device (Ultracel, 100k cutoff, Millipore, Inc.) and centrifuged at 4,000×g for 20 min in a swinging bucket rotor. One hundred μl of PBS was used to rinse the filter and dilute the retentate. The protein concentration was determined using the bicinchoninic acid protein assay (Pierce).

Surface Enhanced Laser Desorption/Ionization Time of Flight Mass Spectrometry (SELDI-TOF-MS)

Normal phase chips (PROTEINCHIP® NP20; Ciphergen Biosystems, Fremont, Calif.), that bind proteins through hydrophilic and charged residues were used for the analysis. Five μl of vesicle preparation was applied in duplicate to the chip and incubated for 30 minutes in a humid chamber. Chips were washed three times with 5 μl high-performance liquid chromatography (HPLC)-grade water and air dried for 10 minutes. Saturated sinapinic acid (SPA, Ciphergen Biosystems, CA) were prepared in 50% acetonitrile/0.5% trifluoroacetic acid according to manufacturers instructions. One μl of matrix solution (SPA) to each spot and air-dried and subsequently read with the PROTEINCHIP® Reader II, (Ciphergen Biosystems) using the following settings: laser intensity 250; detector sensitivity 10; high mass 300 Kda, optimized from 3 Kda to 50 Kda. The data acquisition method was set to automatic laser adjustment and peaks were auto identified from 3 Kda and 50 Kda.

Liquid Chromatography-Tandem Mass Spectrometry (LC-MS/MS)

Collected exosomes were analyzed by LC/MS using an LTQ mass spectrometer (ThermoFinnigan). The pelleted exosomes were first extracted with 2 D gel loading buffer (Q-biosciences) made fresh the day of analysis. The solubilized pellet was then precipitated using four volumes of ice-cold (−20° C.) acetone and incubated overnight at −20° C. The precipitate was collected by centrifugation at 19,200×g. The pellet was dried and re-dissolved into 50 mM ammonium bicarbonate (AmBIC). The protein solution was first reduced using 2 μl of a 500 mM stock of DTT (Q biosciences, single use) at 56° C. for 30 minutes. The solution was then alkylated by adding 2 μl of a 1M stock of iodacetic acid (IAA; Q-biosciences, single use) and incubating at room temperature for 30 minutes in the dark. A fresh vial of trypsin (Promega Gold mass spec grade) was diluted 8 μl to 312 μl in 50 mM AmBic and kept on ice. Ten microliters of the diluted trypsin was then added to the reaction and it was incubated at 37° C. for 4 hours with shaking. Then 50 μl of 0.5% formic acid was added and the mixture was either directly analyzed or stored at −20° C. for analysis. Ten microliters of sample was injected using an automated sampler onto a captrap (Michrom) C18 peptide trap at a flow of 10 μl per min. After 10 min the flow was switched to a 0.5 mm×50 micron C18 column (Michrom).

Peptides were eluted using a linear gradient of 5-40% acetonitrile in water over 50 min. The eluted peptides were directly introduced into an LTQ mass spectrometer using microspray ionization (Michrom ADVANCE™) at a flow rate of approximately 3 µl per min. Samples were analyzed using Excalibur 2.2 software set to analyze ions in a data dependent scanning mode. A precursor scan was followed by data dependent scans of the three most intense ions. Files were searched against a subset of the NR database that included Human and HIV proteins using BioWorks 3.1 (ThermoFinnigan). The threshold for DTA generation was set at 200 and the tolerance for peptides was set at 0.5 Da and proteins at 1.0 Da. Initial protein identification lists were generated using consensus scores of >10.0 and Xcorr scores >1.0.

Electrophoresis and Western Blot

SDS PAGE electrophoresis. Samples were heated at 85° C. for 2 minutes in a Tris-Glycine SDS sample reducing buffer and loaded in a 4-12% CRITERION™ XT Bis-Tris precast acrylamide gel (BioRad, Hercules, Calif.). Approximately 200 ng of sample were loaded into each well. Controls consisted of recombinant HIV Nef (gift of Dr. Andrea Raymond) and HIV recombinant p24 (Immunodiagnostics, Inc.) that were loaded at 30 to 40 ng per well. The gels were stained using Gel Code Blue (Pierce, Inc.) or the proteins were transferred to PVDF membrane (Immobilon-P, Millipore Corp, Billerica, Mass.) for western blot analysis. The SNAP ID system (Millipore, Corp) was used for the western blot analysis for the presence of either HIV Nef or HIV proteins. HIV Nef identification was performed using a monoclonal mouse anti-HIV Nef monoclonal antibody (1:1500, Chemicon Int., CA) and a secondary antibody, goat anti-mouse IgG (H+L) peroxidase conjugated antibody (1:15,000, Jackson Immunoresearch, West Grove, Pa.). HIV proteins were detected using pooled human HIV+ serum (1:15,000) as the primary antibody and a goat anti-human IgG (H+L) peroxidase conjugated antibody (1:15,000, Jackson Immunoresearch). The membrane was incubated with a chemiluminescent substrate (SuperSignal West Femto Maximum, Pierce, Inc.) and exposed to X-ray film (CL-XPOSURE™, Kodak) and developed.

Transmission Electron Microscopy

Samples were fixed in 2.5% glutaraldehyde in 0.1M cacodylate buffer for 2 hours at 4 C followed by 2 washes with 0.1M cacodylate buffer, 5 minutes each. The samples were fixed again with 1% osmium tetroxide in 0.1M cacodylate buffer for 1 hour at 4° C. followed by 2 washes with the cacodylate buffer and 3 washes with deionized water, 5 minutes each. Thin sections were cut, stained with 0.5% aqueous uranyl acetate for 2 hours at room temperature, and viewed with a JEOL 1200EX transmission electron microscope.

EXAMPLE 2: ISOLATION OF URINARY VESICLES, ULTRACENTRIFUGATION VERSUS ULTRAFILTRATION

Vesicles from the urine of six (6) different HIV+ patients were isolated by ultracentrifugation or ultrafiltration to determine which of the two methods yielded the greatest amount of protein. The ultrafiltration method consistently isolated more protein (2930 µg median) than the ultracentrifugation method (591 median).

EXAMPLE 3: SELDI-TOF-MS ANALYSIS OF HIV-ASSOCIATED BIOMARKERS IN URINARY EXOSOMES FROM PATIENTS

FIG. 1 is a flow chart showing an embodiment of an exemplary method for detecting HIV-infection or monitoring the progress of HIV-infection in a subject using a urine sample from the subject. Urinary exosomes from patients of various groups were analyzed for the presence of HIV-associated biomarkers by SELDI-TOF-MS. The results are confirmed by LC-MS/MS. Spectrum of SELDI-TOF-MS from representative patients is shown in FIGS. 2-6. Table 1 summarizes HIV-associated proteins that were detected by SELDI-MS and confirmed by LC-MS/MS in different test groups. Table 2 summarizes the urine protein profiles in individual patient.

TABLE 1

HIV-associated proteins detected in urine samples by SELDI-MS

| Patient | MW | Protein |
|---|---|---|
| HIVAN | 10,585 | HIV envelope gp; HIV Protease |
|  | 23,546 | HIV envelope gp; HIV Nef; HIV Vif |
|  | 33,464 | HIV protein gp; mu A03009B12Rik Protein |
|  | 45,632 | HIV envelope gp; HIV pol protein |
|  | 66,587 | HIV envelope gp; HIV Nef; PgD synthase |
|  | 78,942 | Unknown |
| AA HIV | 23,684 | HIV envelope gp; HIV Nef; PgD synthase |
|  | 83,256 | Unknown |
| FSGS | 66,533 | Unknown |
| White HIV | 23,935 |  |

TABLE 2

Urine protein profiles in individual patient

| ID | Diagnosis | Race | CD4 | VL | Nef | Gag | Pol | Protease | Rev | RT | Tat | Vif | pl | p24 | P17 | poly |
|---|---|---|---|---|---|---|---|---|---|---|---|---|---|---|---|---|
| 22 | HIVAN | AA |  |  | X | X | X | X | X |  | X | X | X | X | X |  |
| 27 | HIV/AIDS | AA | 134 | <50 | X |  |  |  |  |  |  |  |  |  |  |  |
| 28 | HIV/AIDS | AA | 134 | 19,800 | X |  |  | X |  | X |  | X |  |  |  |  |
| 30 | HIV/AIDS | AA | <20 | <10,000 | X | X | X | X |  | X | X | X |  | X | X | X |
| 41 | HIV | AA | 440 | 29,187 | X | X | X |  |  |  |  |  |  |  |  |  |
| 46 | HIV | AA | 689 | <50 | X | X | X |  | X | X |  |  |  |  |  |  |
| 62 | HIV | AA | 232 | <50 | X |  |  |  |  |  |  |  |  |  |  |  |
| 63 | HIV/AIDS | AA | 83 | 2,023 | X |  |  |  |  |  |  |  |  |  |  |  |
| 70 | HIV | AA | 990 | <50 | X |  |  |  |  |  |  |  |  |  |  |  |
| 104 | HIV | AA | 313 | 77 | X | X |  |  |  |  |  |  |  |  |  |  |
| 111 | HIV/AIDS | AA | 182 | <50 |  | X | X |  |  |  |  |  |  |  |  |  |

TABLE 2-continued

Urine protein profiles in individual patient

| ID | Diagnosis | Race | CD4 | VL | Nef | Gag | Pol | Protease | Rev | RT | Tat | Vif | pI | p24 | P17 | poly |
|---|---|---|---|---|---|---|---|---|---|---|---|---|---|---|---|---|
| 112 | HIV | AA | 584 | <200 |  |  | X |  |  | X |  |  |  |  |  |  |
| 48 | HIV | W | 454 | 52000 | X |  |  |  | X |  | X | X |  |  |  |  |
| 86 | HIV | W | 1642 | <75 | X | X | X | X |  |  |  |  |  |  |  |  |
| 103 | HIV | W | 560 | 150 | X | X | X |  |  |  |  |  |  |  |  |  |
| 106 | HIV | W | 302 | <50 |  |  |  |  |  |  |  |  |  |  |  |  |
| 108 | HIV | W | 653 | <50 | X | X | X |  |  |  |  |  |  |  |  |  |
| 110 | HIV | W | 379 | <50 | X | X |  |  |  |  |  |  |  |  |  |  |

Transmission Electron Microscopy (TEM)

TEM was used to visualize the patients' vesicles from urine. Exosomes were isolated from 4 ml of urine, fixed and embedded for TEM. The figure shows distribution of vesicles in: A) HIVAN; B) focal segmental glomerulosclerosis; C) AA HIV+; and D) white HIV+; E) AA HIV negative. HIVAN, FSGS and AA HIV+ patients clearly have a higher population of vesicles compared to white HIV+ patients and AA normal patients.

Ingenuity Pathways Analysis

As shown in Examples 1 and 2, the SELDI-TOF-MS peaks of AA HIV+ patients exhibited exceedingly similar protein patterns to those of HIVAN patients and slightly similar patterns to FSGS patients, suggesting that the AA HIV+ patients whose peaks were similar to those of HIVAN may be predisposed to developing HIVAN. The baseline protein value (30-2000 mg/dl) for the FSGS patients and AA HIV+ patients was in the same range. Similar to the protein values for HIVANb, but unlike FSGS patients, the proteins detected in AA HIV+ patients were analogous to those of HIVAN patients. This underscores the significance that HIV infection, with or without the presence of renal disease, is still largely responsible for development of HIVAN; and a prior condition of renal insufficiency before HIV infection is not a necessary prerequisite for the development of HIVAN.

Unlike AA HIV+ patients, protein profiles of white HIV+ patients were a stark contrast to the protein profiles of HIVAN patients. It suggests that factors other than simple infection of renal cells or the infiltration of infected immune cells in renal tissue probably mediate the expression of nephropathy. The number of AA HIV+ and HIVAN (12/15) patients that had detectable Nef using LC-MS/MS piggybacks on the earlier assertion about the similarities between the kidney pathologies of transgenic mice expressing Nef and HIVAN patients, hinting that Nef may be involved in causing kidney damage to HIV patients. This may explicate the relationship, if any, between the similarity in the kidney pathology of transgenic mice expressing Nef and HIVAN patients, and the similarity between the expression of Nef in the protein profiles of AA HIV+ and HIVAN patients. It may also shed additional insight as to what role Nef plays in the pathogenesis of HIVAN. HIV envelope gp was also detected by LC-MS/MS in HIVAN and AA HIV+ patients. Although local HIV infection of the kidney may have implications beyond development of HIVAN, with kidney serving as a potential viral reservoir, a corollary would be that some of these viruses in the reservoir would find their way in the urine.

The transmission electron microscopy (FIG. 7) shown in the urine of AA HIV+, FSGS and HIVAN patients' conspicuous vesicles were not evident in the urine of white HIV+ and AA normal patients. The HIVAN exosome solution was diluted 10 fold because the initial visualization expressed an exceedingly dense population of exosomes that was difficult to visualize, suggesting that HIVAN patients may be producing vesicles at an increasing rate than all the other patient groups. The HIV-associated kidney damage may responsible for this marked increase in exosome excretion in AA HIV+ and HIVAN patients.

EXAMPLE 4: WESTERN BLOT ANALYSIS, VALIDATION OF THE PRESENCE OF HIV NEF AND OTHER HIV PROTEINS

Figure 8:
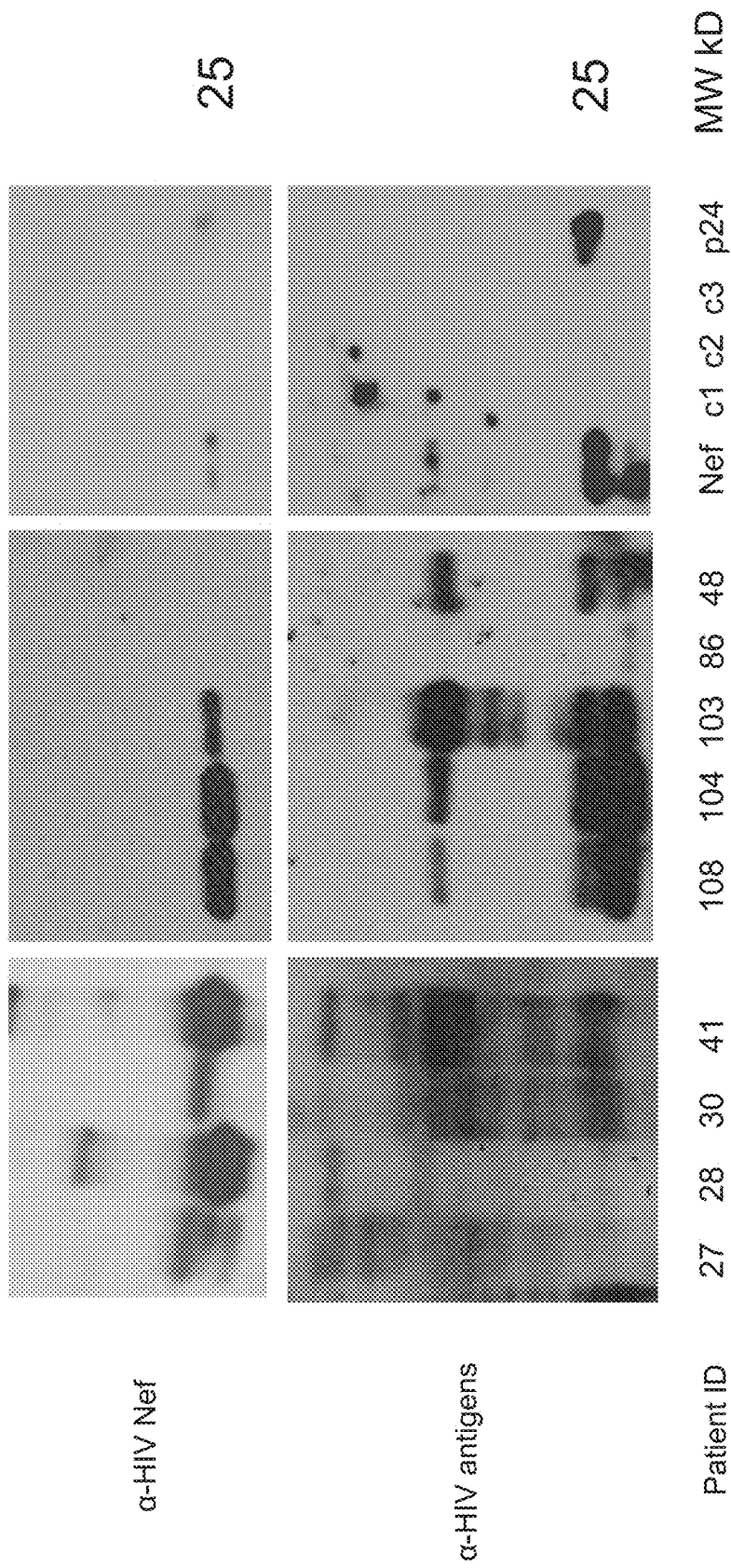
FIG. 8 is a composite of pictures showing Western blot analysis of urinary vesicles from HIV+ patients and controls. Vesicles were isolated from urine by ultrafiltration and analyzed for the presence of HIV Nef or other HIV proteins. The top panel used anti-HIV Nef monoclonal antibodies, while the lower panel utilized pooled HIV+ patient sera s the primary antibodies. Patients 27, 28, 30, 41 and 104 were AA. Patients 108, 103, 86 and 48 were HIV+ white patients. The last panel is control panel for three HIV negative individuals, recombinant HIV Nef and p24.

Urinary vesicle samples from fourteen (14) HIV+AA and nine (9) HIV+ white patients were isolated using ultrafiltration and analyzed for the presence of HIV Nef and other HIV proteins using western blot analysis. All the HIV+AA samples were positive for HIV Nef by western blot, although HIV Nef was not detected in sample 41 by mass spectrometry (FIG. 8). This discrepancy could be caused by the isolation method utilized for the mass spectrometry analysis, which was ultracentrifugation, and yields less protein. HIV Nef was only identified in four (4) HIV+ white patients while mass spectrometry identified three (3) samples without HIV Nef. All HIV+ patients had detectable HIV proteins by western blots, but had varying kinds and amounts (FIG. 8).

EXAMPLE 5: SANDWICH ELISA ANALYSIS OF HBV BIOMARKERS IN URINARY EXOSOMES FROM PATIENTS

Exosome ELISA

The Nunc 96 strip well ELISA plates coated with 100 ul of µg/ml GNA and blocked with Blocking Buffer were washed 1× with 250 µl of Wash Buffer (0.1% Tween-20 in PBS). Positive controls (mannan from S. cerevisiae) and samples were added to the plates in the amount of 100 µl/well and incubated for 1 hour at room temperature. The plates were washed 1× with 250 µl of Wash Buffer. 100 µl of HRP labeled GNA (1 ug/ml) or an antibody specific to a marker on the exosome of interest were added to each well and incubated for 1 hour at room temperature. The plates were washed 4× with 250 µl of Wash Buffer. 100 µl of Tetramethylbenzidine (TMB) were added to each well and incubated for 30 minutes at room temperature or until the Blank well begins to show color. The reaction was stopped by adding 100 µl of 1M $H_2SO_4$ to each well. The plates were read in an ELISA plate reader at 450 nm. Serial dilution of samples or antibodies was made with Diluent Buffer (1% BSA, 0.1% Tween-20 in PBS). Marker specific-antibodies include the following:

Anti-Hepatitis C NS4b antigen antibody, mouse monoclonal (MA1-7358, Thermo Scientific);

Anti-Hepatitis C NS3 antigen antibody, mouse monoclonal (MA1-7357, Thermo Scientific);

Anti-Hepatitis C Core antigen antibody, mouse monoclonal (ab2582, Abcam);

Anti-Hepatitis C Core antigen antibody, mouse monoclonal (MA1-080, Thermo Scientific);

Anti-Hepatitis C NS3 antigen antibody, mouse monoclonal (MA1-21376, Thermo Scientific);

Anti-Hepatitis C NS4 antigen antibody, mouse monoclonal (MA1-91550, Thermo Scientific);

Anti-Hepatitis C NS5a antigen antibody, mouse monoclonal (MA1-7368, Thermo Scientific);

Anti-Hepatitis A virus antibody, goat polyclonal (LS-C103171, Lifespan Biosciences);

Anti-Hepatitis B virus antibody, goat polyclonal (LS-05624, Lifespan Biosciences);

Anti-ALG6 (alpha-1,3-glucosyltransferase or Dolichyl pyrophosphate Man9GlcNAc2 alpha-1,3-glucosyltransferase) antibody—mouse monoclonal, recombinant fragment: SYSGAGKPPM FGDYEAQRHW QEITFNLPVK QWYFNSSDNN LQYWGLDYPP LTAYHSLLCA YVAKFINPDW IALHTSRGYE SQAHKLFMRT (SEQ ID NO: 1), corresponding to amino acids 25-115 of Human ALG6 (ab57112, Abcam);

Anti-ALG6 antibody—rabbit polyclonal, Synthetic peptide corresponding to a region within N terminal amino acids 36-85 (GDYEAQRHWQ EITFNLPVKQ WYFNSSDNNL QYWGLDYPPL TAYHSLLCAY; SEQ ID NO:2) of human ALG6 (NP_037471) (ab80873, Abcam); and Anti-ALG3 (alpha-1,3-mannosyltransferase or Dolichyl-P-Man:Man(5)G1cNAc(2)-PP-dolichyl mannosyltransferase) antibody—rabbit polyclonal, Recombinant fragment, corresponding to amino acids 69-122 of Human ALG3 (ab151211, Abcam).

EXAMPLE 6: SANDWICH ELISA ANALYSIS OF HBV BIOMARKERS IN URINARY EXOSOMES FROM PATIENTS

Urinary exosomes isolated from hepatitis patients and normal controls were analyzed for the presence of hepatitis A virus (HAV), hepatitis B virus (HBV) and hepatitis C virus (HCV)-associated biomarkers by exosome ELISA.

Figure 9:
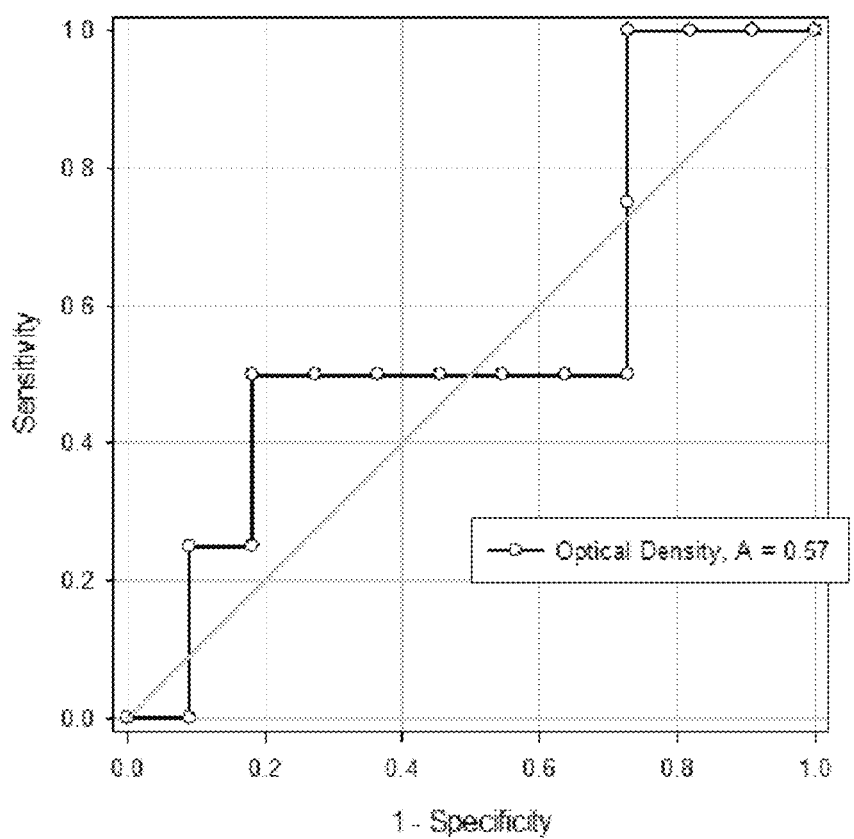
FIG. 9 is a receiver operating characteristic (ROC) curve for hepatitis B diagnosis based on exosome ELISA.

FIG. 9 shows the receiver operating characteristic (ROC) curve for diagnosis of hepatitis B using anti-Hepatitis B antibody in the exosome ELISA.

Figure 10:
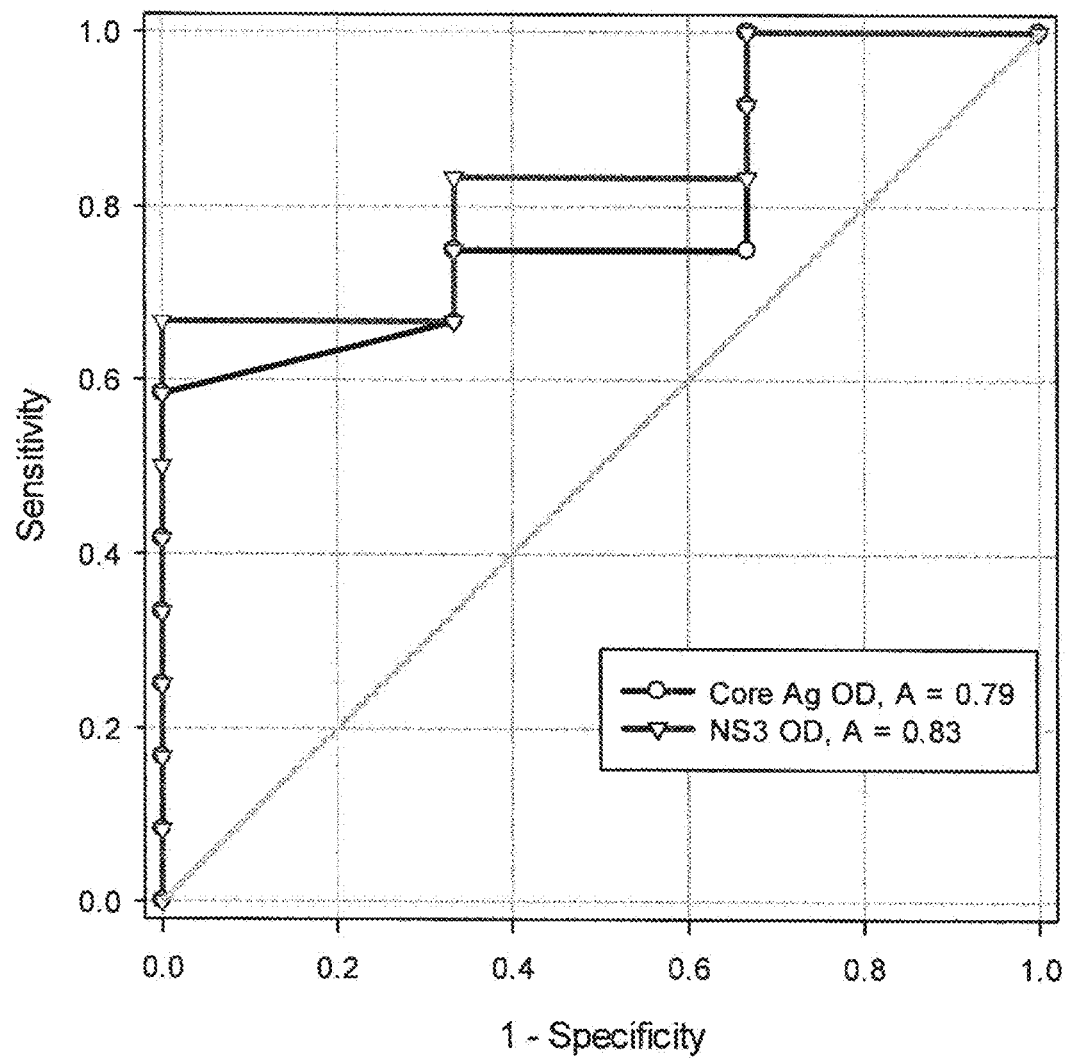
FIG. 10 is a ROC curve for hepatitis C diagnosis based on exosome ELISA.

FIG. 10 is a ROC curve for diagnosis of hepatitis C using HCV core antigen and HCV NS3 protein as the biomarkers for hepatitis C in the exosome ELISA.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following embodiments. The embodiments are intended to cover the components and steps in any sequence which is effective to meet the objectives there intended, unless the context specifically indicates the contrary.

---

What is claimed is:

1. A method for diagnosing human immunodeficiency virus (HIV) infection in a subject, comprising:
   (a) contacting a urine sample with a first binding agent specific for an exosomal marker, wherein the first binding agent is attached to a solid surface and captures exosomes in the urine sample removed from the subject;
   (b) contacting the captured exosomes in step (a) with a second binding agent specific for an HIV protein selected from the group consisting of Nef, HIV envelope gp120, HIV protease, Vif, Pol, Gag, Gag-pol, Rev, reverse transcriptase (RT), Tat, p1, p17, Vpu, Vpr, gp41 and DNA polymerase; and
   (c) detecting a presence or absence of the HIV protein in the captured exosomes,
   wherein the presence of the HIV protein in step (c) is indicative of an HIV infection in the subject, and wherein the absence of the HIV protein in step (c) is indicative of the absence of HIV infection in the subject.

2. The method of claim 1, wherein the solid surface comprises a plate.

3. The method of claim 1, further comprising the step of administering a therapeutic drug for HIV infection if the HIV protein is detected in step (c).

4. The method of claim 1, wherein the first binding agent comprises a lectin.

5. The method of claim 4, wherein the lectin is selected from the group consisting of Lens culinaris agglutinin (LCA), Galanthus nivalis lectin (GNA), Narcissus pseudonarcissus lectin (NPL), Allium sativum lectin (ASA), Lens culinaris lectin (LCH), Sambucus nigra lectin (SNA), Maackia amurensis lectin (MAL), Concanavalin A (Con A), Aleuria aurantia lectin (AAL), Lotus tetragonolobus lectin (LTL), Naja mossambica lectin (NML), Dolichos biflorus agglutinin (DBA), Helix aspersa lectin (HAL), Psophocarpus tetragonolobus lectin II (PTL II), Wisteria floribunda lectin (WFL), Erythrina cristagalli lectin (ECL), Griffonia simplicifolia lectin II (GSL II) and Phaseolus vulgaris leucoagglutinin (PHA-L).

6. The method of claim 1, wherein the first binding agent comprises an antibody.

7. The method of claim 6, wherein the antibody is an anti-ALG6 (alpha-1,3-glucosyltransferase) antibody.

8. A method for monitoring the course of HIV infection in a subject, comprising:
   (a) obtaining a first urine sample removed from the subject at a first time point and a second urine sample removed from the subject at a second time point;
   (b) contacting the first urine sample and the second urine sample with a first binding agent specific for an exosomal marker, wherein the first binding agent is attached to a solid surface and captures exosomes in the first and second urine samples removed from the subject;
   (c) contacting the captured exosomes in step (h) with a second binding agent specific for an HIV protein selected from the group consisting of Nef, HIV envelope gp120, HIV protease, Vif, Pol, Gag, Gag-pol, Rev, reverse transcriptase (RT), Tat, p1, p17, Vpu, Vpr, gp41 and DNA polymerase;
   (d) measuring levels of the HIV protein in the captured exosomes in the first urine sample and the second urine sample; and
   (e) determining the progression of HIV infection between the first time point and the second time point based on the result of step (d).

9. The method of claim 8, wherein a the solid surface comprises a plate.

10. The method of claim 8, further comprising the step of administering a therapeutic drug for HIV infection if the HIV protein is detected in each of the first and second urine samples.

11. The method of claim 8, wherein the first binding agent comprises a lectin.

12. The method of claim 11, wherein the lectin is selected from the group consisting of Lens culinaris agglutinin (LCA), Galanthus nivalis lectin (GNA), Narcissus pseudonarcissus lectin (NPL), Allium sativum lectin (ASA), Lens culinaris lectin (LCH), Sambucus nigra lectin (SNA), Maackia amurensis lectin (MAL), Concanavalin A (Con A), Aleuria aurantia lectin (AAL), Lotus tetragonolobus lectin (LTL), Naja mossambica lectin (NML), Dolichos biflorus agglutinin (DBA), Helix aspersa lectin (HAL), Psophocarpus tetragonolobus lectin II (PTL II), Wisteria floribunda lectin (WFL), Erythrina cristagalli lectin (ECL), Griffonia simplicifolia lectin II (GSL II) and Phaseolus vulgaris leucoagglutinin (PHA-L).

13. The method of claim 8, wherein the first binding agent comprises an antibody.

14. The method of claim 13, wherein the antibody is an anti-ALG6 (alpha-1,3-glucosyltransferase) antibody.

15. A method for monitoring the effectiveness of treatment to a subject with an anti-HIV agent, comprising:
   (a) administering an anti-HIV agent to the subject and obtaining first and second urine samples from the subject at first and second time points relative to the administration;
   (b) contacting the first urine sample and the second urine sample with a first binding agent specific for an exosomal marker, wherein the first binding agent is attached to a solid surface and captures exosomes in the first and second urine samples;
   (c) contacting the captured exosomes in step (b) with a second binding agent specific for an HIV protein selected from the group consisting of Nef, HIV envelope gp120, HIV protease, Vif, Pol, Gag, Gag-pol, Rev, reverse transcriptase (RT), Tat, p1, p17, Vpu, Vpr, gp41 and DNA polymerase;
  (d) measuring levels of the HIV protein in the captured exosomes in the first urine sample and the second urine sample; and
  (e) determining the effectiveness of treatment between the first time point and the second time point based on the result of step (d).

16. The method of claim 15, wherein the solid surface comprises a plate.

17. The method of claim 15, further comprising the step of administering a therapeutic drug for HIV infection if the HIV protein is detected in the first and second urine samples.

18. The method of claim 15, wherein the first binding agent comprises a lectin.

19. The method of claim 18, wherein the lectin is selected from the group consisting of Lens culinaris agglutinin (LCA), Galanthus nivalis lectin (GNA), Narcissus pseudonarcissus lectin (NPL), Allium sativum lectin (ASA), Lens culinaris lectin (LCH), Sambucus nigra lectin (SNA), Maackia amurensis lectin (MAL), Concanavalin A (Con A), Aleuria aurantia lectin (AAL), Lotus tetragonolobus lectin (LTL), Naja mossambica lectin (NML), Dolichos biflorus agglutinin (DBA), Helix aspersa lectin (HAL), Psophocarpus tetragonolobus lectin II (PTL II), Wisteria floribunda lectin (WFL), Erythrina cristagalli lectin (ECL), Griffonia simplicifolia lectin II (GSL II) and Phaseolus vulgaris leucoagglutinin (PHA-L).

20. The method of claim 15, wherein the first binding agent comprises an antibody, wherein the antibody is an anti-ALG6 (alpha-1,3-glucosyltransferase) antibody.

* * * * *